(12) United States Patent
Mast et al.

(10) Patent No.: US 10,070,852 B2
(45) Date of Patent: *Sep. 11, 2018

(54) LATERAL RETRACTOR SYSTEM AND METHODS OF USE

(71) Applicant: Zimmer Biomet Spine, Inc., Westwinster, CO (US)

(72) Inventors: Randall G. Mast, Denver, CO (US); Alan R. Burkholder, Denver, CO (US); Andrew Schifle, Superior, CO (US); Adam Kanter, Gibsonia, PA (US); David O. Okonkwo, Pittsburgh, PA (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/802,031

(22) Filed: Nov. 2, 2017

(65) Prior Publication Data

US 2018/0055504 A1    Mar. 1, 2018

Related U.S. Application Data

(63) Continuation of application No. 15/183,380, filed on Jun. 15, 2016, which is a continuation of application
(Continued)

(51) Int. Cl.
  *A61B 1/32* (2006.01)
  *A61B 17/02* (2006.01)
  (Continued)

(52) U.S. Cl.
  CPC ........ *A61B 17/0206* (2013.01); *A61B 17/025* (2013.01); *A61B 17/7079* (2013.01);
  (Continued)

(58) Field of Classification Search
  CPC .................. A61B 1/313; A61B 1/3135; A61B 2017/0218; A61B 1/32; A61B 17/02;
  (Continued)

(56) References Cited

U.S. PATENT DOCUMENTS 832,201 A    10/1906    Kistler
972,983 A    10/1910    Arthur
(Continued)

FOREIGN PATENT DOCUMENTS

EP    0792620 B1    5/2000
EP    1146822 B1    9/2003
(Continued)

OTHER PUBLICATIONS

English translation of FR1005345 (A).
(Continued)

*Primary Examiner* — Lynnsy Summitt
(74) *Attorney, Agent, or Firm* — Schwegman Lundberg & Woessner, P.A.

(57) ABSTRACT

Technology disclosed herein relates to retractors and methods of use for surgical procedures, and in particular, spinal surgical procedures. In one embodiment, a surgical retractor includes a pair of pivotable armatures and a translatable armature. A body for supporting the armatures is provided, with a handle connected thereto. The handle includes a first rotary actuator, wherein a rotation of the first rotary actuator moves the pair of pivotable armatures in opposite arcuate directions, and a second rotary actuator, wherein a rotation of the second rotary actuator translates the translatable at nature in a linear direction.

20 Claims, 28 Drawing Sheets

Related U.S. Application Data

No. 13/601,887, filed on Aug. 31, 2012, now Pat. No. 9,572,560.

(60) Provisional application No. 61/529,756, filed on Aug. 31, 2011.

(51) Int. Cl.
    *A61B 17/70*     (2006.01)
    *A61B 17/00*     (2006.01)

(52) U.S. Cl.
    CPC ........... *A61B 2017/00477* (2013.01); *A61B 2017/0256* (2013.01)

(58) Field of Classification Search
    CPC ........... A61B 17/0206; A61B 17/0218; A61B 2017/0237; A61B 17/3439; A61B 17/025; A61B 2017/0256; A61B 17/0293; A61B 17/3423; A61B 17/0281
See application file for complete search history.

(56) References Cited

U.S. PATENT DOCUMENTS

| | | | |
|---|---|---|---|
| 1,328,624 A | 1/1920 | Graham | |
| 1,331,737 A | 2/1920 | Emil | |
| 1,400,648 A | 12/1921 | Whitney | |
| 2,374,863 A | 5/1945 | Guttmann | |
| 4,616,635 A | 10/1986 | Caspar et al. | |
| 4,926,849 A | 5/1990 | Downey | |
| 5,097,820 A | 3/1992 | Shulman et al. | |
| 5,616,117 A | 4/1997 | Dinkler et al. | |
| 5,697,889 A | 12/1997 | Slotman et al. | |
| 5,776,054 A | 7/1998 | Bobra | |
| 5,928,139 A | 7/1999 | Koros et al. | |
| 5,976,171 A | 11/1999 | Taylor | |
| D422,705 S | 4/2000 | Koros et al. | |
| 6,073,343 A | 6/2000 | Petrick et al. | |
| 6,074,343 A | 6/2000 | Nathanson et al. | |
| 6,139,493 A | 10/2000 | Koros et al. | |
| D448,081 S | 9/2001 | Koros et al. | |
| 6,322,500 B1 * | 11/2001 | Sikora | A61B 17/0206 600/219 |
| 6,348,036 B1 | 2/2002 | Looney et al. | |
| 6,416,468 B2 | 7/2002 | Deckman et al. | |
| 7,491,168 B2 | 2/2009 | Raymond et al. | |
| 7,819,801 B2 | 10/2010 | Miles et al. | |
| 7,909,846 B1 | 3/2011 | Taylor et al. | |
| 7,922,658 B2 | 4/2011 | Cohen et al. | |
| 7,976,463 B2 | 7/2011 | Dewey et al. | |
| 7,988,625 B2 | 8/2011 | Abdelgany et al. | |
| 8,062,218 B2 | 11/2011 | Sebastian et al. | |
| 8,137,284 B2 | 3/2012 | Miles et al. | |
| 8,353,826 B2 | 1/2013 | Weiman | |
| 8,357,184 B2 | 1/2013 | Woolley et al. | |
| 8,409,087 B2 | 4/2013 | Ames et al. | |
| 8,480,576 B2 | 7/2013 | Sandhu | |
| 8,636,655 B1 | 1/2014 | Childs | |
| 8,636,656 B2 | 1/2014 | Nichter et al. | |
| 8,702,600 B2 | 4/2014 | Perrow | |
| 8,764,649 B2 | 7/2014 | Miles et al. | |
| 8,827,900 B1 | 9/2014 | Pimenta | |
| 9,572,560 B2 | 2/2017 | Mast et al. | |
| 9,579,095 B2 | 2/2017 | Perrow | |
| 9,826,966 B2 | 11/2017 | Mast et al. | |
| 9,943,301 B2 | 4/2018 | Mast et al. | |
| 2003/0149341 A1 | 8/2003 | Clifton et al. | |
| 2004/0254428 A1 | 12/2004 | Ritland | |
| 2005/0055031 A1 | 3/2005 | Lim | |
| 2005/0113644 A1 | 5/2005 | Obenchain et al. | |
| 2005/0159650 A1 | 7/2005 | Raymond et al. | |
| 2005/0159651 A1 | 7/2005 | Raymond et al. | |
| 2005/0215862 A1 | 9/2005 | Larson et al. | |
| 2007/0027363 A1 | 2/2007 | Gannoe et al. | |
| 2007/0073111 A1 | 3/2007 | Bass | |
| 2007/0100212 A1 | 5/2007 | Pimenta et al. | |
| 2007/0208227 A1 | 9/2007 | Smith et al. | |
| 2007/0260261 A1 | 11/2007 | Runco et al. | |
| 2008/0300465 A1 | 12/2008 | Feigenwinter et al. | |
| 2009/0018399 A1 | 1/2009 | Martinelli | |
| 2009/0062619 A1 | 3/2009 | Bjork et al. | |
| 2009/0156902 A1 | 6/2009 | Dewey et al. | |
| 2009/0203969 A1 | 8/2009 | Cohen et al. | |
| 2010/0036384 A1 | 2/2010 | Gorek et al. | |
| 2010/0105987 A1 | 4/2010 | Miles et al. | |
| 2010/0130827 A1 | 5/2010 | Pimenta et al. | |
| 2010/0174147 A1 | 7/2010 | Miles et al. | |
| 2010/0222644 A1 | 9/2010 | Sebastian et al. | |
| 2011/0098535 A1 | 4/2011 | Pimenta et al. | |
| 2011/0130793 A1 | 6/2011 | Woolley et al. | |
| 2011/0224497 A1 | 9/2011 | Weiman et al. | |
| 2011/0301422 A1 | 12/2011 | Woolley et al. | |
| 2012/0046527 A1 | 2/2012 | Cianfrani et al. | |
| 2012/0172669 A1 | 7/2012 | Loftus et al. | |
| 2012/0245431 A1 * | 9/2012 | Baudouin | A61B 17/0206 600/213 |
| 2012/0245432 A1 | 9/2012 | Karpowicz et al. | |
| 2012/0253132 A1 | 10/2012 | Davis | |
| 2012/0283521 A1 | 11/2012 | Smith et al. | |
| 2012/0296171 A1 | 11/2012 | Lovell et al. | |
| 2013/0158359 A1 | 6/2013 | Predick et al. | |
| 2013/0190575 A1 | 7/2013 | Mast et al. | |
| 2013/0261401 A1 | 10/2013 | Hawkins et al. | |
| 2013/0274557 A1 | 10/2013 | Bowman et al. | |
| 2014/0018633 A1 | 1/2014 | Woolley et al. | |
| 2014/0058206 A1 | 2/2014 | Pimenta et al. | |
| 2014/0058210 A1 | 2/2014 | Raymond et al. | |
| 2014/0066719 A1 | 3/2014 | Nichter | |
| 2014/0135584 A1 | 5/2014 | Lee et al. | |
| 2014/0148650 A1 | 5/2014 | Miles et al. | |
| 2014/0148652 A1 | 5/2014 | Weiman | |
| 2014/0288378 A1 | 9/2014 | Miles et al. | |
| 2014/0350347 A1 | 11/2014 | Karpowicz et al. | |
| 2016/0051242 A1 | 2/2016 | Predick et al. | |
| 2016/0296220 A1 | 10/2016 | Mast et al. | |
| 2016/0317137 A1 | 11/2016 | Predick et al. | |
| 2017/0086812 A1 | 3/2017 | Mast et al. | |
| 2017/0340318 A1 | 11/2017 | Mast et al. | |

FOREIGN PATENT DOCUMENTS

| | | |
|---|---|---|
| EP | 1146829 B1 | 3/2005 |
| EP | 2750611 B1 | 11/2016 |
| FR | 1005345 A | 4/1952 |
| WO | WO-2005060837 A2 | 7/2005 |
| WO | WO-2005096735 A2 | 10/2005 |
| WO | WO-2008121421 A1 | 10/2008 |
| WO | WO-2012040206 A1 | 3/2012 |
| WO | WO-2013033630 A1 | 3/2013 |

OTHER PUBLICATIONS

"U.S. Appl. No. 13/601,887, Examiner interview Summary dated Jan. 26, 2015", 3 pgs.

"U.S. Appl. No. 13/601,887, Final Office Action dated Apr. 21, 2015", 15 pgs.

"U.S. Appl. No. 13/601,887, Non Final Office Action dated Nov. 3, 2014", 22 pgs.

"U.S. Appl. No. 13/601,887, Non Final Office Action dated Nov. 23, 2015", 23 pgs.

"U.S. Appl. No. 13/601,887, Non Final Office Action dated Mar. 15, 2016", 14 pgs.

"U.S. Appl. No. 13/601,887, Response filed Jan. 26, 2015 to Non Final Office Action dated Nov. 3, 2014", 17 pgs.

"U.S. Appl. No. 13/601,887, Response filed Feb. 17, 2016 to Non Final Office Action dated Nov. 23, 2015", 9 pgs.

"U.S. Appl. No. 13/601,887, Response filed Jul. 21, 2015 to Final Office Action dated Apr. 21, 2015", 12 pgs.

"U.S. Appl. No. 15/183,380, Non Final Office Action dated Jun. 1, 2017", 8 pgs.

"U.S. Appl. No. 15/183,380, Preliminary Amendment filed Sep. 9, 2016", 8 pgs.

(56) References Cited

OTHER PUBLICATIONS

"U.S. Appl. No. 15/183,380, Response filed Jun. 26, 2017 to Non Final Office Action dated Jun. 1, 2017", 10 pgs.
"U.S. Appl. No. 15/183,380, Response filed Sep. 6, 2017 to Notice of Non-Complinat dated Jul. 6, 2017", 7 pgs.
"U.S. Appl. No. 15/372,426, Non Final Office Action dated Mar. 7, 2017", 12 pgs.
"U.S. Appl. No. 15/372,426, Notice of Allowance dated Jun. 16, 2017", 9 pgs.
"U.S. Appl. No. 15/372,426, filed May 8, 2017 to Non-Final Office Action dated Mar. 7, 2017", 11 pgs.
"European Application Serial No. 12827679.7, Extended European Search Report dated May 8, 2015", 7 pgs.
"European Application Serial No. 12827679.7, Office Action dated Mar. 8, 2014", 3 pgs.
"European Application Serial No. 16198215.2, Partial European Search Report dated Jun. 8, 2017", 13 pgs.
"International Application Serial No. PCT/US2012/053519, International Preliminary Report on Patentability dated Mar. 13, 2014", 6 pgs.
"International Application Serial No. PCT/US2012/053519, International Search Report dated Jan. 29, 2013", 5 pgs.
"International Application Serial No. PCT/US2012/053519, Written Opinion dated Jan. 29, 2013", 4 pgs.
"U.S. Appl. No. 15/680,744, Preliminary Amendment filed Aug. 21, 2017", 6 pgs.
"U.S. Appl. No. 15/183,380, Examiner Interview Summary dated Jan. 11, 2018", 3 pgs.
"U.S. Appl. No. 15/183,380, Final Office Action dated Nov. 13, 2017", 9 pgs.
"U.S. Appl. No. 15/183,380, Response filed Jan. 15, 2018 to Final Office Action dated Nov. 13, 2017", 10 pgs.
"U.S. Appl. No. 15/372,426, Corrected Notice of Allowance dated Nov. 3, 2017", 2 pgs.
"U.S. Appl. No. 15/680,744, Examiner Interview Summary dated Jan. 10, 2018", 3 pgs.
"U.S. Appl. No. 15/680,744, Non-Final Office Action dated Nov. 17, 2017", 15 pgs.
"European Application Serial No. 16198215.2, Extended European Search Report dated Sep. 29, 2017", 11 pgs.
"U.S. Appl. No. 15/183,380, Notice of Allowance dated Feb. 23, 2018", 8 pgs.
"U.S. Appl. No. 15/680,744, filed Feb. 15, 2018 to Non-Final Office Action dated Nov. 17, 2017", 11 pgs.
"U.S. Appl. No. 15/680,744, Final Office Action dated Mar. 15, 2018", 20 pgs.
"U.S. Appl. No. 15/921,431, Preliminary Amendment filed Mar. 15, 2018", 7 pgs.

\* cited by examiner

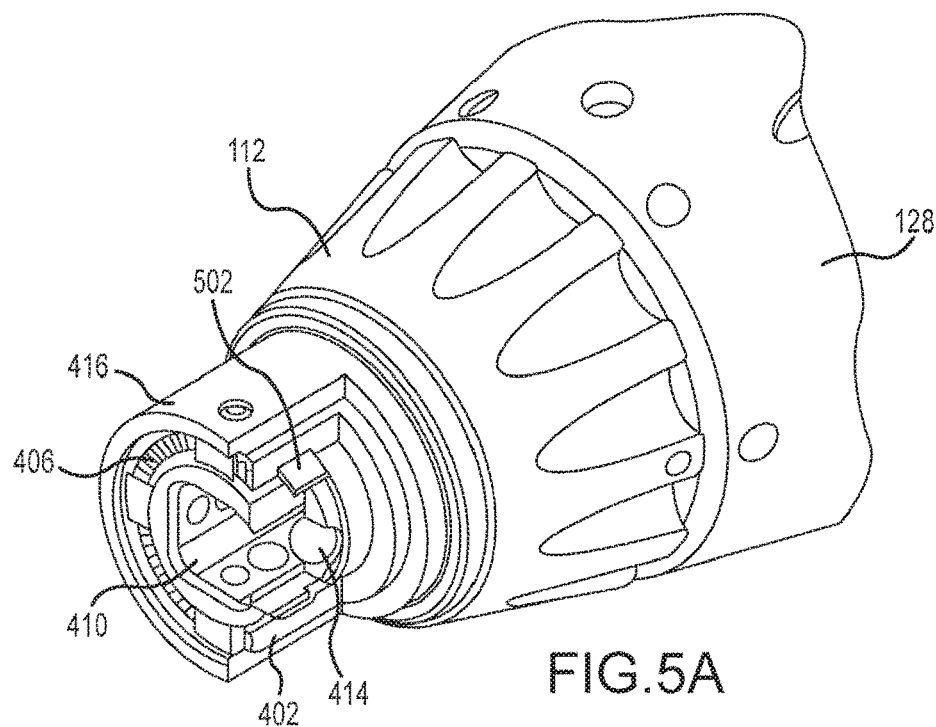
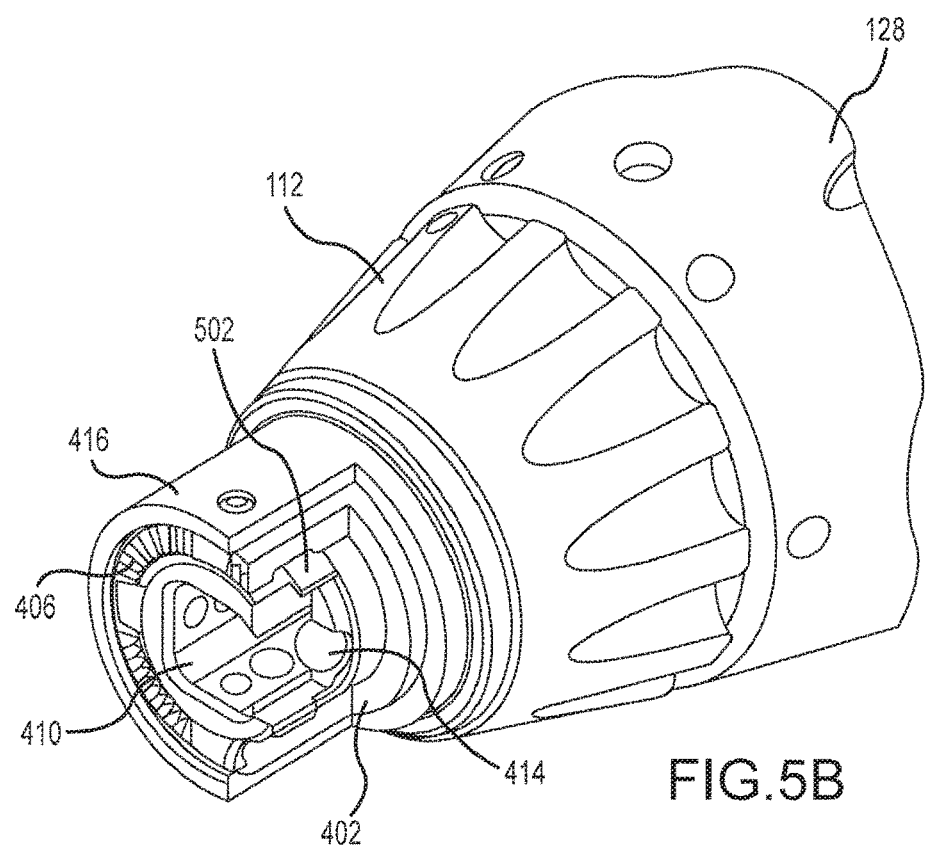

LATERAL RETRACTOR SYSTEM AND METHODS OF USE

CROSS-REFERENCE TO RELATED APPLICATIONS

This application is a continuation of U.S. patent application Ser. No. 15/183,380, filed on Jun. 15, 2016, which is a continuation of U.S. patent application Ser. No. 13/601,887, filed on Aug. 31, 2012, which claims priority to and the benefit of U.S. Provisional Application Ser. No. 61/529,756, filed Aug. 31, 2011, entitled, "Lateral Retractor System and Methods of Use, " the disclosures of which are hereby incorporated by reference herein in their entireties.

INTRODUCTION

Current retractor systems for lateral spine surgical procedures create an opening through the side of a patient, and may pass through the psoas muscle. Improved systems are desirable with respect to at least ease of use, stability, visibility and robustness.

SUMMARY

In one aspect, the technology relates to retractors and methods of use for surgical procedures, and in particular, spinal surgical procedures. In one embodiment, a surgical retractor includes a pair of pivotable armatures and a translatable armature. A body for supporting the armatures is provided, with a handle connected thereto. The handle includes a first rotary actuator, wherein a rotation of the first rotary actuator moves the pair of pivotable armatures in opposite arcuate directions, and a second rotary actuator, wherein a rotation of the second rotary actuator translates the translatable armature in a linear direction.

In one embodiment, a method of creating a distraction corridor to a surgical site is disclosed. The method includes providing a surgical retractor having a handle comprising two rotatable elements, and a plurality of blades moveable relative to the handle. The method includes inserting the plurality of blades simultaneously into a body tissue; actuating a first of the two rotatable elements so as to separate at least two of the plurality of blades; and actuating a second of the two rotatable elements so as to translate at least one of the plurality of blades.

BRIEF DESCRIPTION OF THE DRAWINGS

There are shown in the drawings, embodiments which are presently preferred, it being understood, however, that the technology is not limited to the precise arrangements and instrumentalities shown.

FIGS. 5A-5C depict enlarged partial perspective views of a locking element in various positions.

DETAILED DESCRIPTION

Figure 1:
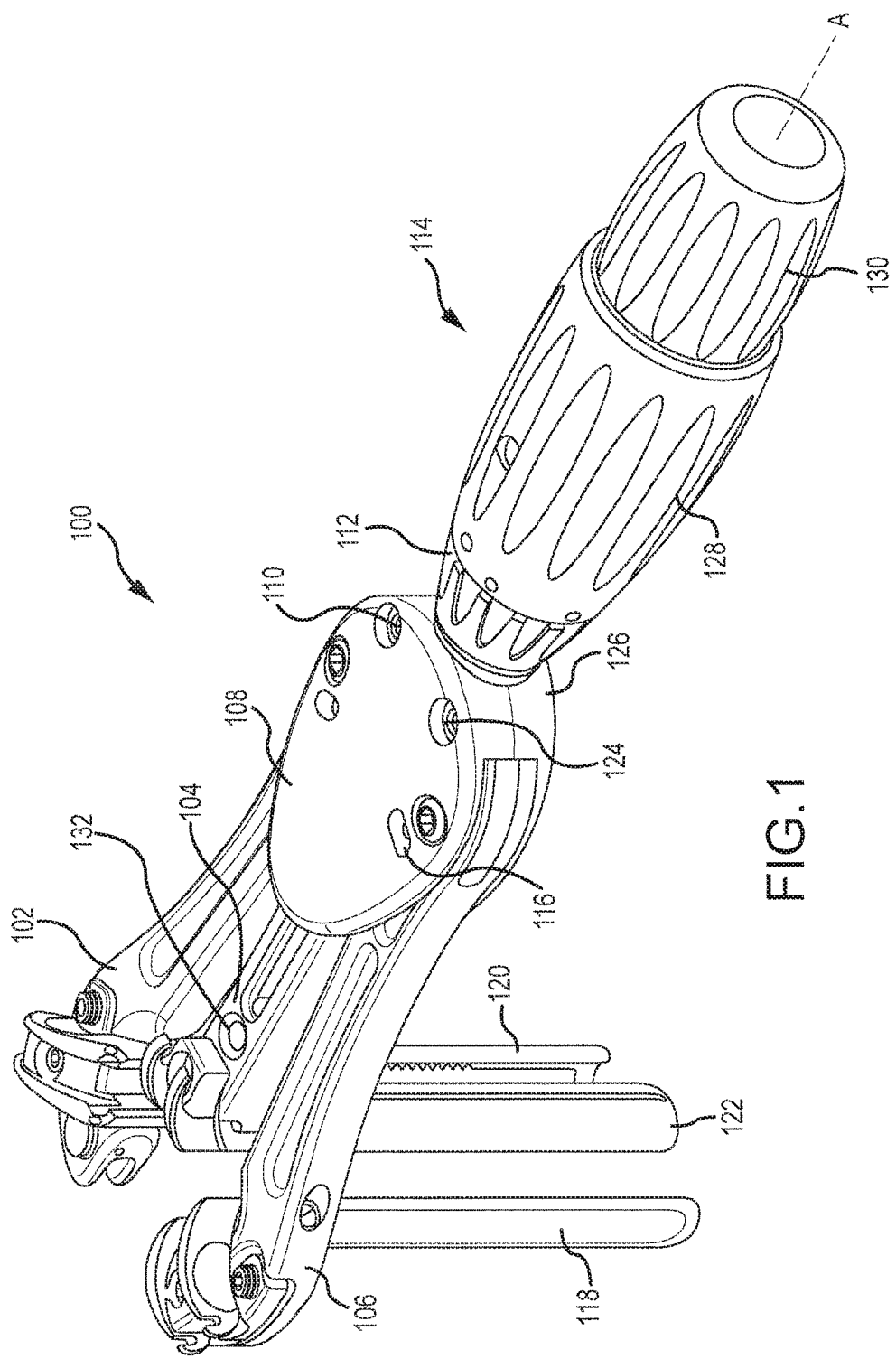
FIG. 1 depicts a perspective view of a retractor device in an open position.

FIG. 1 depicts a retractor device 100 that includes a main retractor body 126, a handle 114, and a plurality of armatures (arms) 102-106 with blades 118-122 attached thereto. The retractor body 126 includes a number of components that drive the operable elements of the retractor device 100. The arms 102-106 may be opened and closed by rotating actuators 128, 130 on the handle 114. The blades 118-122 attached to each arm 102-106 are used to form a surgical distraction corridor in a body tissue. This corridor is enlarged as the arms 102-106 are opened. These and other elements of the retractor device 100 are described in more detail below.

In the depicted embodiment, the retractor body 126 includes a top cover plate 108 and a bottom cover plate (not seen in FIG. 1) that limit access to the drive elements located therein. The top cover 108 plate includes one or ore slots 116. In some embodiments, each of the two pivoting arms 102, 106 is connected to a guide pin (not seen in FIG. 1). The pin is located within the slot 116, and restricts movement of the arm 102, 106 to which it is connected as the arm 102, 106 is opened and closed. In the depicted embodiment, a slot 116 is associated with each of the pivoting arms, with two pins and slots 116 operating together to restrict the movement of arms 102, 106. In other embodiments, only a single slot 116 may be used. In certain embodiments, the slot(s) 116 may be entirely eliminated. Inclusion of the slot 116, however, helps control the connection between the pivoting arm 102, 106 and the retractor body 126. One or more articulating arm connection points 110, 124 may also be located on the top cover 108. These connection points 110, 124 may be used to connect the retractor device 100 to a discrete articulating aim that is connected to a surgical table or other substantial element. Rigid connection of the retractor device 100 to the surgical table or other fixed structure allows the device 100 to be held in place, so the surgeon may be free to perform other aspects of a procedure without having to hold the retractor device 100.

The retractor body 126 is connected to a handle 114 that may be disengageable, as described below. In the depicted embodiment, the handle 114 includes two rotatable actuators 128, 130 that are used to actuate the arms of the retractor device 100. In some embodiments, rotation of the main retractor actuator 128 (centrally located on the handle 114 in the depicted embodiment) actuates the two pivoting arms (i.e., the cranial and caudal arms 102, 106). In some embodiments, rotation of the posterior actuator 130 (located at the end of the handle 114 in the depicted embodiment) actuates the posterior arm 104. In alternative embodiments, the position of the actuators 128, 130 may be switched or otherwise vary. In other embodiments, each armature has a separate handle rotatable actuator to allow the armatures to be opened individually. In still other embodiments, the handle contains a single rotatable actuator that actuates all of the armatures simultaneously. The rotational axis A is shared by both the main retractor actuator 128 and the posterior actuator 130. In alternative embodiments, other actuator elements may be used. In one example, the actuator element for the pivoting arms may be a circular disc having an axis of rotation substantially orthogonal to the axis A of the handle 114. The disc may be connected to a worm gear, lead screw (FIG. 2), or other element within the handle 114 that operates the pivoting arms 102, 106. A similar disc may be used for the posterior arm 104. Alternatively, a translating element, for example a slide movable parallel to the axis of the handle 114, may be used to actuate the posterior arm 104. As described in more detail below, some or all of the handle 114 may be removably connected to the retractor body 126. A connection element 112 may connect the handle 114 to the retractor body 126. In certain embodiments, the connection element 112 incorporates a lock having multiple positions and functions as described below with regard to FIGS. 5A-5C.

In some embodiments, retractor 100 includes three arms 102-406 used to help form a surgical distraction corridor in a body tissue. In some cases, arms 102-406 include two pivoting arms 102, 106 and one translating arm 104, with each or some having a blade 118-122 extending therefrom. A first end of each of the pivoting arms 102, 106 is attached to the retractor body 126. The opposite end of each arm 102, 106 is secured to a blade 118, 120 that inserted into the body tissue. For certain embodiments, such as when retractor 100 is used in a lateral spinal surgical procedure, the terms "cranial" and "caudal" may be associated with certain arms 102, 106 and blades 118, 120 to help identify their position relative to the patient. For example, arm 102 and blade 120 may be referred to as caudal arm 102 and caudal blade 120. Similarly, arm 106 and blade 118 may be referred to as a cranial arm 106 and cranial blade 118. In that regard, the cranial blade 118 is located on the side of the retractor 100 closest to the head of the patient, while the caudal blade 120 is located on the side of the retractor 100 closest to the legs. The cranial and caudal blades 118, 120 are similarly configured, such that either blade 118, 120 may be considered either the cranial or caudal blade, depending on which side the patient is laying during a surgical procedure. In one embodiment, both pivoting arms 102, 106 (and therefore both blades 118, 120), pivot in an arcuate direction away from a centerline of the retractor device 100, defined by the axis A of the handle 114, as the main actuator 128 is rotated. Of course, other embodiments of the retractor device may be configured such that separate actuators are used for each of the two pivoting arms 102, 106. Using a single actuator for both pivoting blades 118, 120, however, helps ensure even opening of the surgical corridor during use and a balancing of forces against the blades 118, 120.

The translating arm 104 has first and second ends, with the first end connected to the main retractor body 126 and the second end connected to a blade 122. The translating arm 104 may be referred to as the posterior arm 104 and is configured to move axially along the axis A. That is, the arm 104 may be drawn into and extended out of the retractor body 126, as the posterior actuator 130 is actuated. The posterior arm 104 may also include an articulating arm connection element 132, thereby providing an additional point of connection of the retractor device 100 to the surgical table or other secure structure. The posterior blade 122 is secured to the translating arm 104, either directly or with a pivotable connection as described above with regard to the blades 118, 120. Additionally, although the device 100 is typically utilized such that the handle 114 is pointed toward the surgeon, the device 100 may also be oriented so that the handle 114 is pointed away from the surgeon during use. In that case, the translating arm 104 may be referred to as an anterior arm 104.

Figure 2:
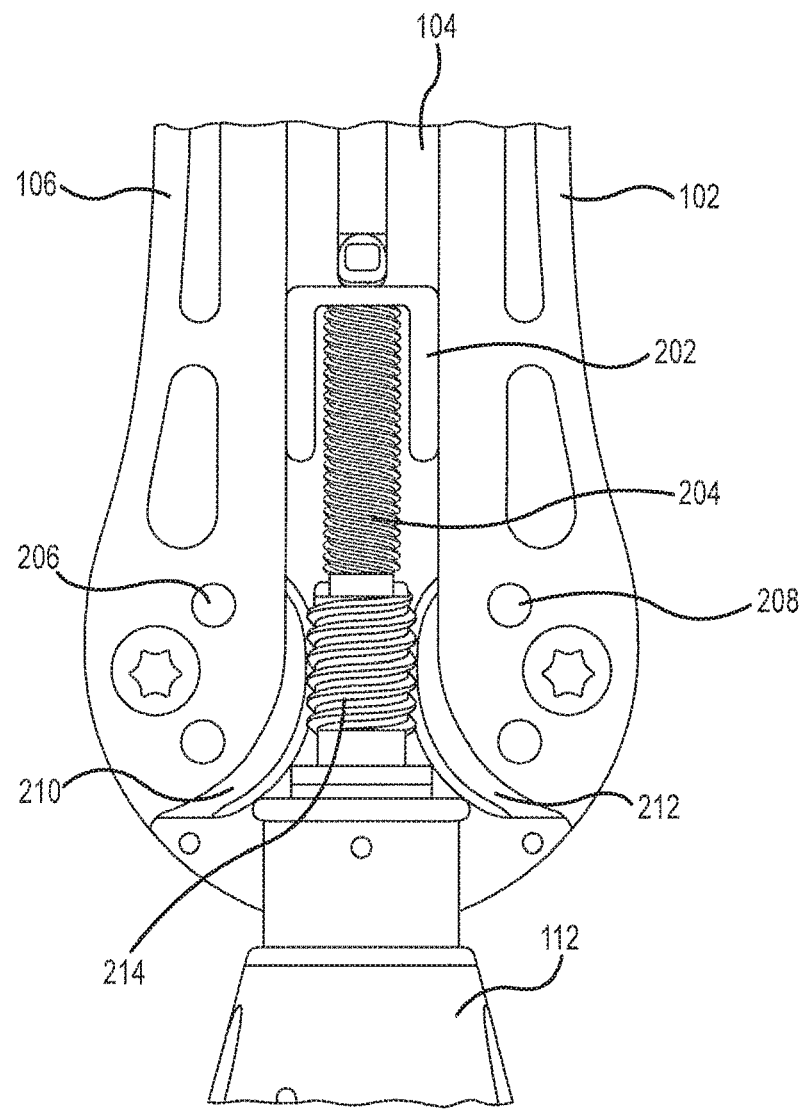
FIG. 2 depicts a partial enlarged top view of a retractor device with a top cover removed.

FIG. 2 depicts an embodiment of the drive mechanisms for opening and closing the arms 102-106 of the retractor device 100. As shown, a main worm drive mechanism 214 or lead screw is used to actuate the cranial and caudal arms 102, 106. Rotation of the main worm drive 214 by the main actuator 128 (not shown) rotates the main worm gears 210, 212, thereby separating or pivoting the cranial and caudal arms 102, 106. In some embodiments, worm drive 214 engages teeth on worm gears 210, 212. In one embodiment, the use of a worm drive mechanism 214 to separate the cranial 118 and caudal blades 120 allows for a large number of open positions between the blades 118, 120. In some cases, the worm drive mechanism 214 provides an unlimited number of open positions depending on the amount of rotation of main worm drive 214. Additionally, the blades 118, 120 are brought together using the worm drive mechanism 214. In other words, the worn in driver 214 and worm gear mechanisms 210, 212 prevent the cranial arm 102 and caudal arm 106 from moving unless specifically actuated. In this manner, the blades 118, 120 are maintained in a desired position until the worm drive mechanism 214 is actuated to further open or close the blades 118, 120. A posterior drive element may be a lead screw 204 mechanism that is engaged with a lead nut 202 to the translating arm 104, allowing for movement of the translating arm 104. In the depicted retractor device 100, the shaft that connects the lead screw 204 to the posterior actuator 130 passes through the main worm drive 214 that activates the cranial and caudal arms 102, 106. As with the worm drive 214, forces applied directly to the posterior blade 122 or arm 104 will not move those elements, compared to a ratchet-type or other system.

Figure 3A:
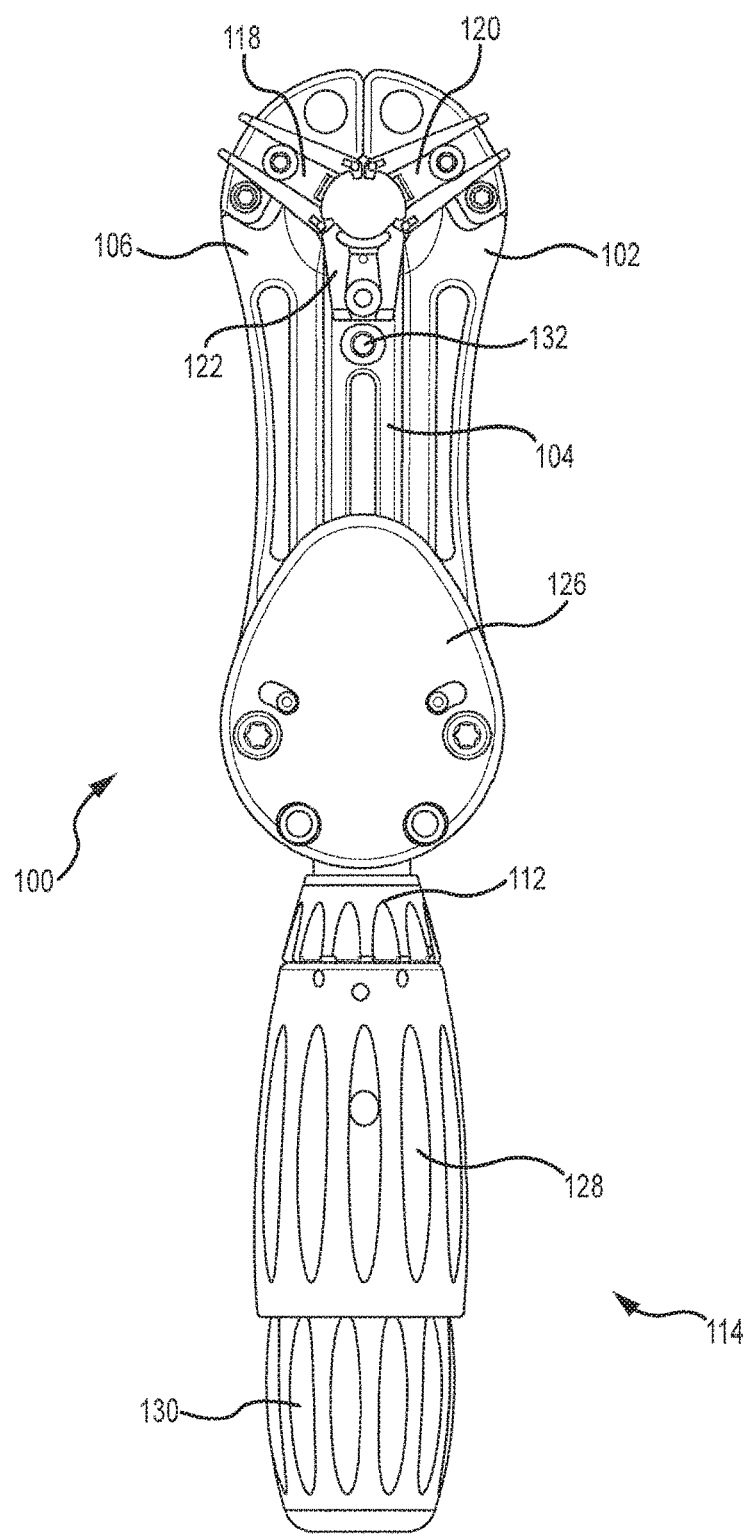
FIG. 3A depicts a top view of a retractor device in a closed position.
Figure 3B:
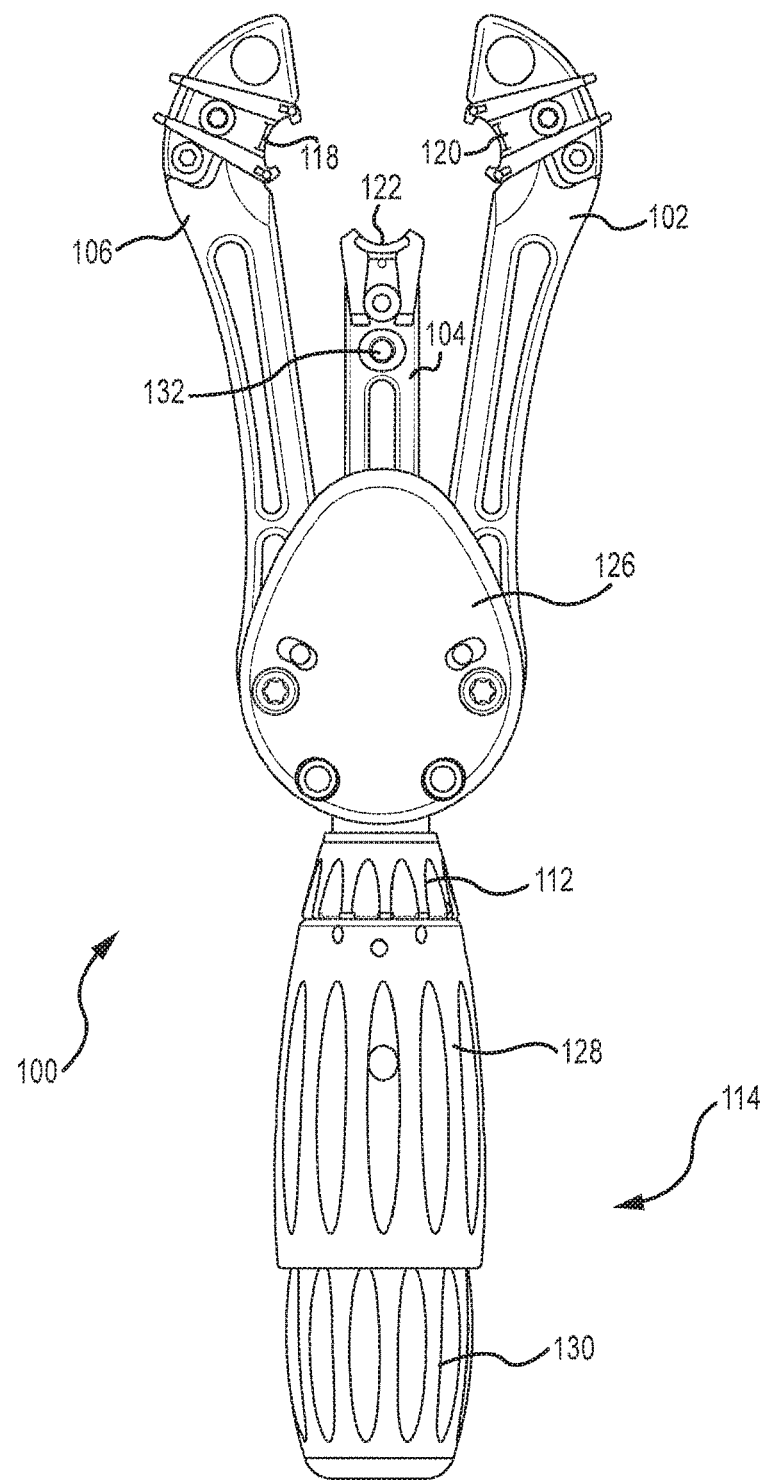
FIG. 3B depicts a top view of a retractor device in an open position.

FIGS. 3A and 3B depict the retractor device 100 in closed and open positions, respectively. When in the closed position, in one embodiment, the blades 118-122 form a perimeter that is configured to surround one or more generally round dilators (FIG. 7) that are first introduced into a body tissue. These dilators and the use thereof, are further described below. The blades 118-122 need not abut one another but may be so configured if desired. Gaps or spaces between the blades 118-122 when in the closed position are generally not a concern unless these gaps are large enough to allow creep of tissue between the blades 118-122. In a particular embodiment, a gap exists between the cranial blade 118 and the caudal blade 120, even when the cranial arm 106 and caudal arm 102 are in a closed and abutting position. In some embodiments the gap extends the entire length of blades 118 and 120. Rotating the main actuator 128 located on the handle 114 moves the arms and the blades 118, 120 away from each other, in arcuate directions. Rotation of the posterior actuator 130 moves the posterior arm 104 and blade 122. When the blades 118-122 are inserted into a body tissue, this movement forces the tissue apart, creating a surgical corridor, the interior of which may be accessed by a surgeon.

Figure 4:
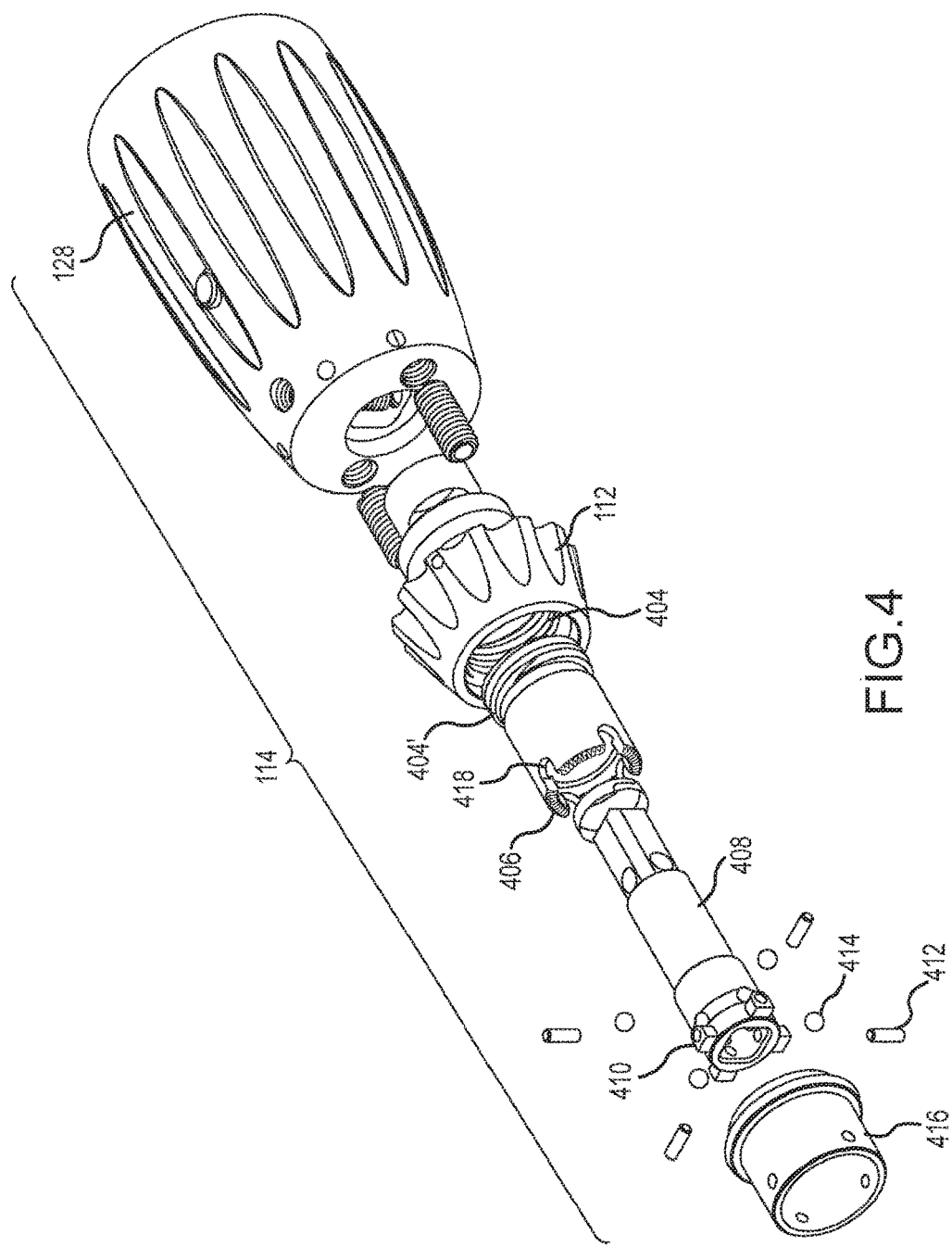
FIG. 4 depicts a partial exploded perspective view of a handle of a retractor device.

FIG. 4 depicts a partial exploded view of an embodiment of the handle 114, specifically, the portion of the handle 114 that actuates the cranial and caudal arms 102, 106. The main actuator 128 portion of the handle 114 is connected to an elongate shaft 408. The connection element/lock 112 includes an internal thread connection 404 that mates with a corresponding thread connection 404' on a friction sleeve 402. Rotation of the connection element/lock 112 rotates the friction sleeve 402. A number of locking elements 406 project from the friction sleeve 402 and engage with a collar 416. As the locking elements 406 engage with the collar 416, functionality of the retractor device 100 changes, as described with regard to FIGS. 5A-5C. Collar 416 is coupled to core 410. In one embodiment, pins 412 couple collar 416 to core 410 and are welded or otherwise affixed in place.

Figure 5C:
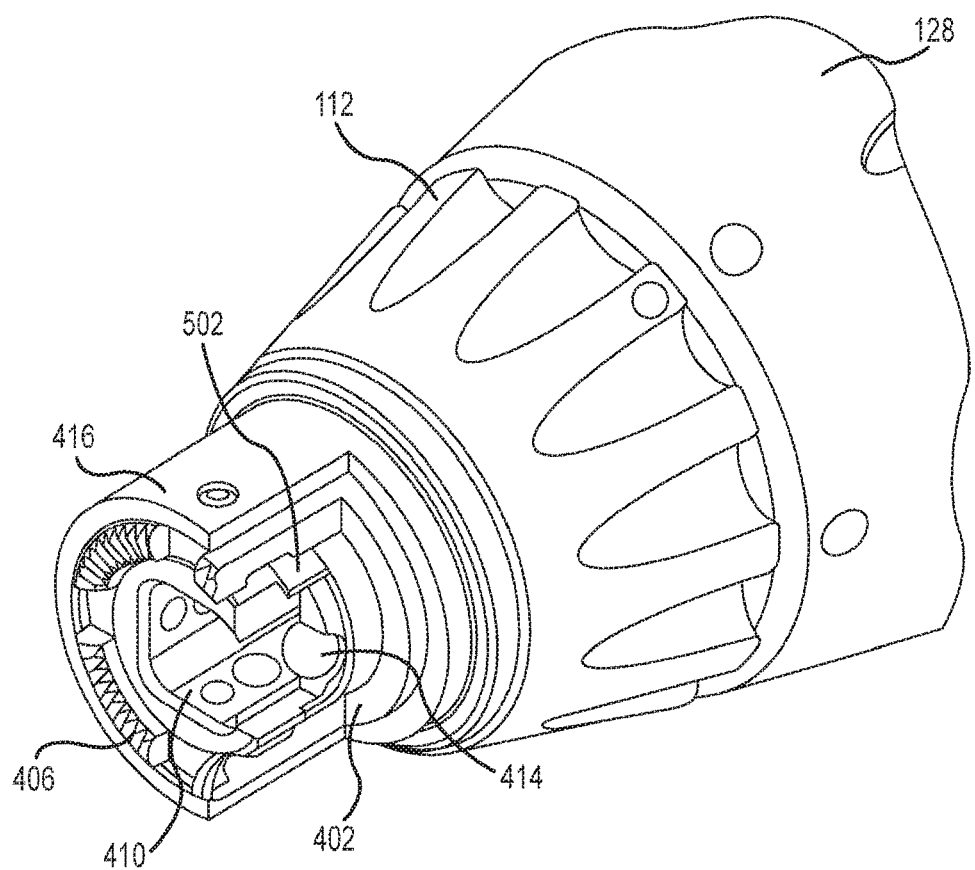

FIG. 5A depicts a first position of the connection element 112, as that element engages with the collar 412. In this position, referred to as a "soft engagement" position, ball bearings 414 are free to move within the constraints of a C-spring 502, because of openings 418 present between the locking elements 406 of the friction sleeve 402. FIG. 5B depicts a second position, wherein the connection element 112 is rotated a desired or set amount, such as about thirty (30) degrees, about forty-five (45) degrees, about sixty (60) degrees, or the like. In this position, the locking elements 406 are moved forward, such that the C-spring 502 is locked out, thereby restricting movement of the ball bearing 414. This position captures the shaft 406 and allows the retractor arms to be opened and closed. FIG. 5C depicts a third position, wherein the connection element 112 is rotated an additional desired or set amount, such as about another thirty (30) degrees, about another forty-five (45) degrees, about another sixty (60) degrees, or the like. This moves the friction sleeve 402, and therefore the locking elements 406, further forward so as to engage a corresponding toothed plate in the retractor body 126. In this position, the friction sleeve 402 is in the fully locked position, such that the gaps 418 are restricting the C-spring 502 from expanding. This locks the ball bearings 414 in place, and the locking elements 406 are in a position where they will interface with the corresponding teeth in the retractor body 126 (not shown). The center core 410, the handle body, and the collar 416 are fixed relative to each other, using a variety of techniques. For example, in one embodiment pins 412 couple collar 416 to core 410.

Figure 6A:
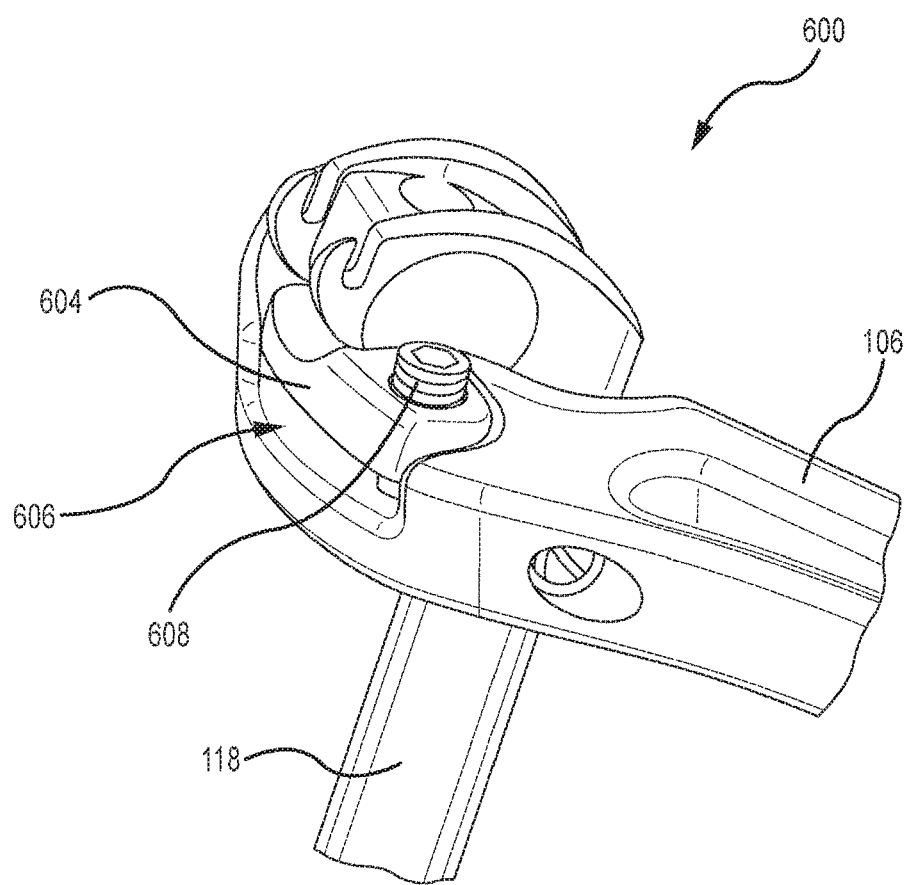
FIGS. 6A-6C depict enlarged partial views of a blade/arm interface of a retractor device.
Figure 6B:
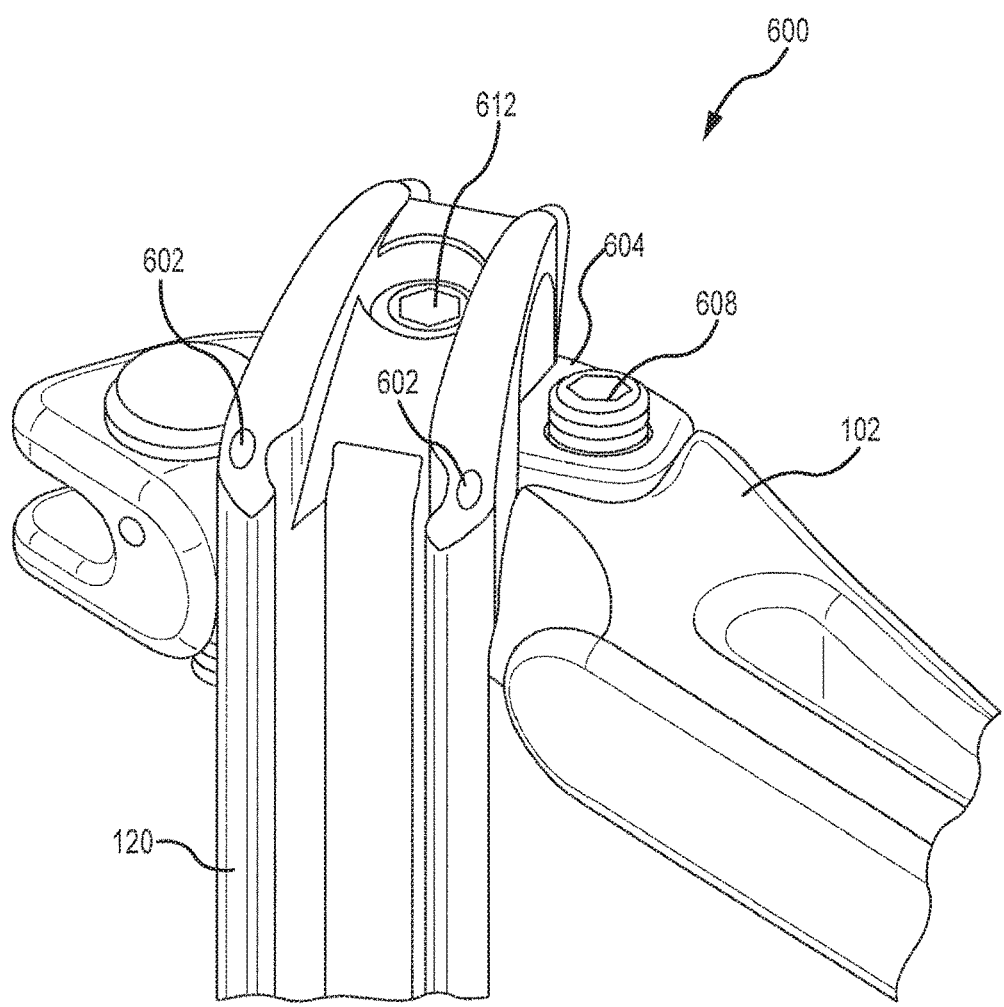
Figure 6C:
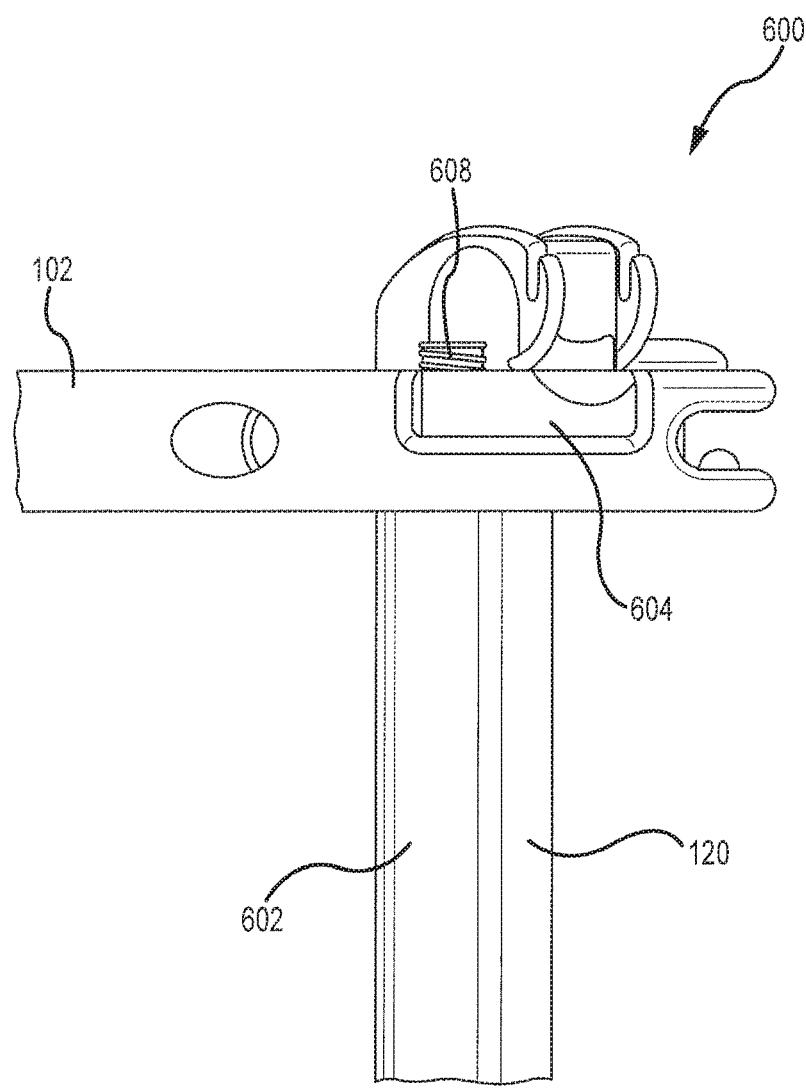

FIGS. 6A-6C depict enlarged partial views of a blade/arm interface 600, and show various technologies incorporated therein. FIG. 6A depicts an end of the cranial arm 106, and blade 118. The blade 118 is pivotably connected to the arm 106, specifically with a blade base 604 that is positionable within a toeing cut-out 606 in the arm 106. In one embodiment, blade 118 has a curved proximal end which engages the blade base portion of arm 106. The blade base 604, in one embodiment, is rotatably coupled to arm 106. In this embodiment, a blade attachment mechanism, depicted in FIG. 6B as a screw 612, threads through a hole in blade 118 proximal end and into a threaded opening in the top of blade base 604. Once blade 118 is coupled to the blade base 604 of arm 106, rotation of the blade base 604 allows the distal end of blade 118 to be toed in a desired direction as described below. In a particular embodiment, a toeing screw 608 is coupled to the blade base 604. Rotation of toeing screw 608 causes movement of the blade base 604 relative to arm 106. In a particular embodiment, toeing screw 608 extends through a threaded hole in blade base 604. Further rotation of toeing screw 608 causes the tip portion of screw 608 to engage toeing cut-out 606 and thereafter provide for rotation of the blade base 604 relative to cut-out 606. In this manner, blade 118 also rotates, which allows the distal end of the blade 118 to move past its initial orientation that is generally orthogonal to the arm 106. In certain embodiments, each of the cranial and caudal blades may be toed up to about ten (10) degrees, up to about twenty (20) degrees, or up to about thirty (30) degrees from orthogonal. In a preferred embodiment, the toeing of blades 118, 120 allows the distal ends of blades 118, 120 to be toed outwards, providing a larger opening near the operative site. Regardless of the maximum toeing angle, the toeing screw 608 allows for infinite degrees of variability across the entire range of motion. In certain embodiments, the posterior blade (not shown) may be toed as well, although the posterior blade 122 typically does not have toeing ability. This toeing functionality may also be incorporated into the caudal arm 102, as depicted in FIG. 6B. While the depicted embodiment shows blade 118 proximal end coupled to a rotatable blade base 604, in another embodiment the proximal end of blade 118 includes structure for providing the rotation function. In this manner, the blade 118 is firmly coupled to the arm 106, but provides the rotation for a controlled toeing function.

FIG. 6B also depicts one or more channels 602 on the blade 120 that each may receive a probe, a K-wire, a stimulation electrode, or the like. In some embodiments, the stimulation electrode may be used to detect the location, and/or proximity of nerves in the target area, which may help avoid damage to the nerves. FIG. 6C depicts a rear perspective view of the caudal blade 120 of FIG. 6B. The channel 602 for receiving the probe may be a substantially open slot along a rear face of the blade 118, as depicted in FIG. 6C. In general, the channel 602 may extend to a distal end of the blade 118, such that the electrode may detect the location and/or proximity of any nerves once it is advanced into the tissue. Of course, channels 602 may be located elsewhere on the blade 118 as well. In certain embodiments, the channel 602 extends along only a portion of the length of the blade 118, or is not present at all. In some embodiments, the channel 602 has a jog, a bend, or a narrowed region along at least portion of the length of channel 602. In some embodiments, the jog or bend is near the distal end of blade 118. In this manner, the elongated flexible element, such as a K-wire or probe, inserted into the channel 602 is at least partly held in place within channel 602 due to the increased friction needed to move the flexible element relative to the jog, bend or narrowed portion. This feature may be useful, for example, to help maintain the flexible element within channel 602 while blade 118 is being inserted or removed from the patient tissue.

Figure 7:
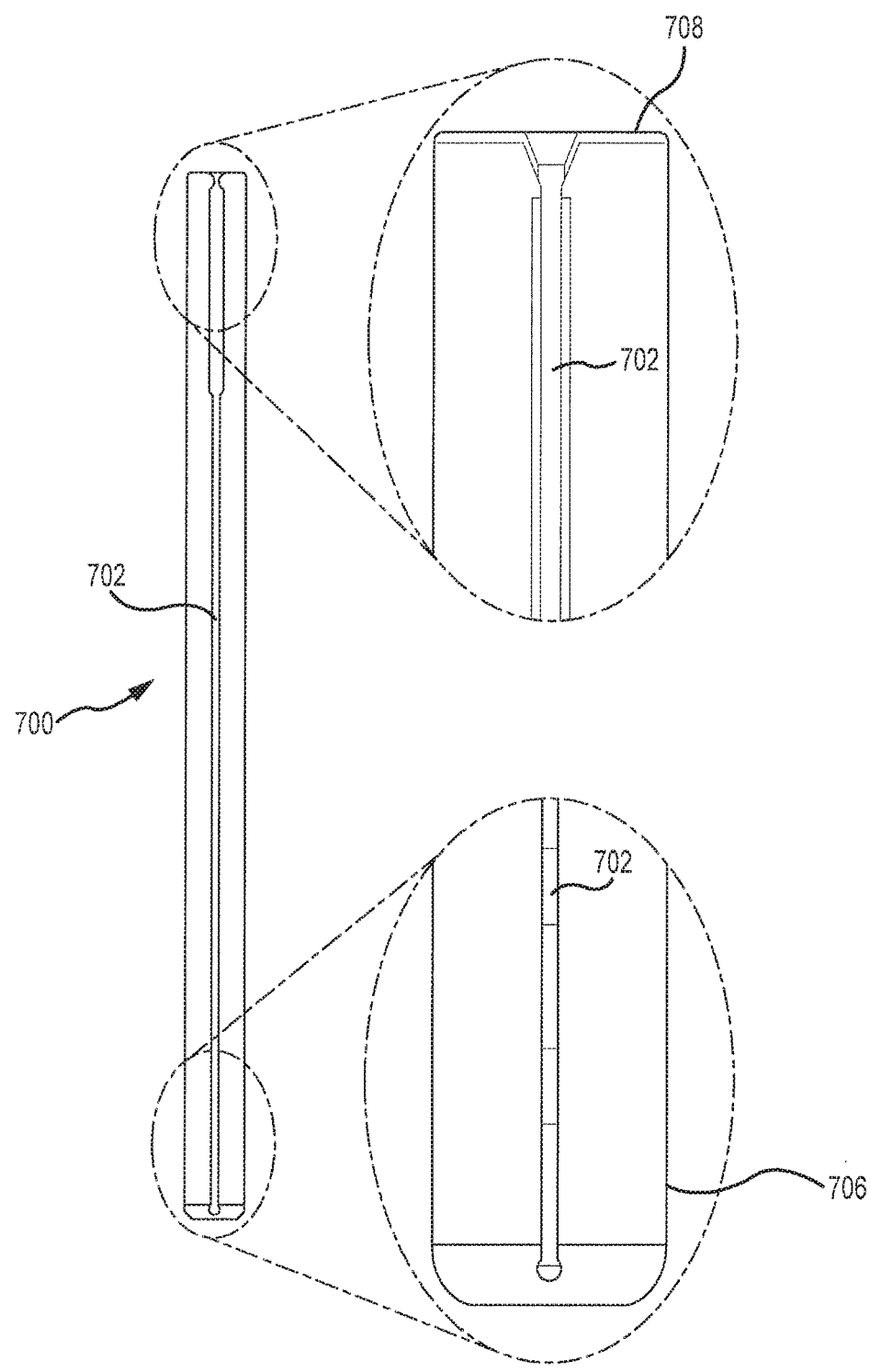
FIG. 7 depicts a side view and enlarged partial side views of a dilator.

FIG. 7 depicts side and enlarged partial side views of a dilator 700 that may be used in conjunction with the retractor depicted herein. One or more dilators 700 may be used to further increase a diameter of an initial distraction corridor as described in more detail below. Similar to the channel located on the retractor blade(s), a channel 702 may also be located on the dilator(s) 700, and may be sized to accommodate a stimulation electrode, a probe, or other elongate element. In certain embodiments, a single stimulating electrode may be used with each component (e.g., a first dilator, a second dilator, retractor blade) introduced into the body tissue. After insertion of the first dilator, the electrode may be withdrawn and inserted into a channel of a next dilator, then into a channel in a retractor blade, until the blades are opened, thereby creating the desired surgical corridor. In some embodiments, a top surface 708 of the proximal end 704 may be constructed of hardened material to allow the dilator 700 to be impacted with an object such as a hammer during insertion. In a particular embodiment, dilator 700 comprises anodized aluminum, with the proximal end 704 comprising a steel impaction cap. In this manner, the proximal end may be struck with a hammer or other impaction tool with little to no deformation of proximal end 704. In some embodiments, proximal end 704 may be flared (much like the head of a nail). At least a portion of the distal end 706 may be tapered to ease insertion into the initial distraction corridor.

Figure 8A:
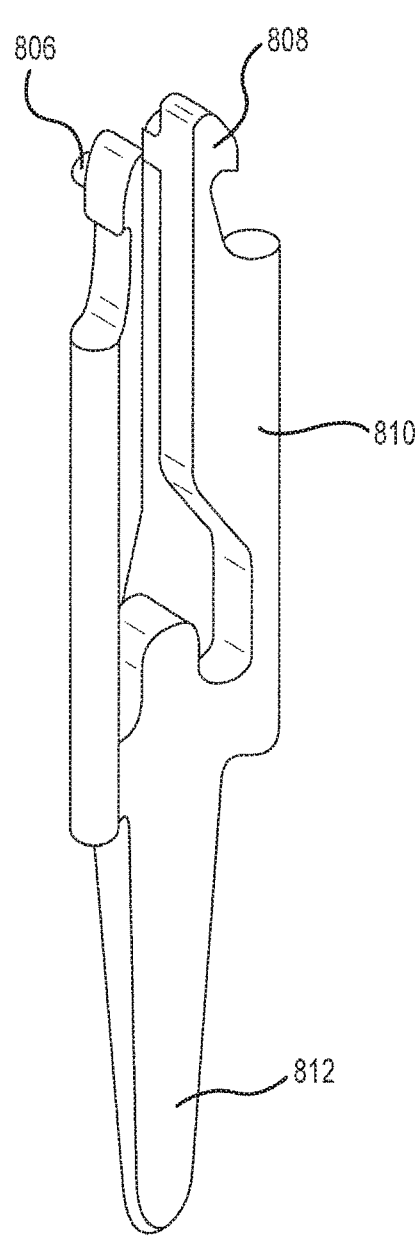
FIGS. 8A and 8B depict a perspective view of an intradiscal shim, and the intradiscal shim extending from a blade, respectively.
Figure 8B:
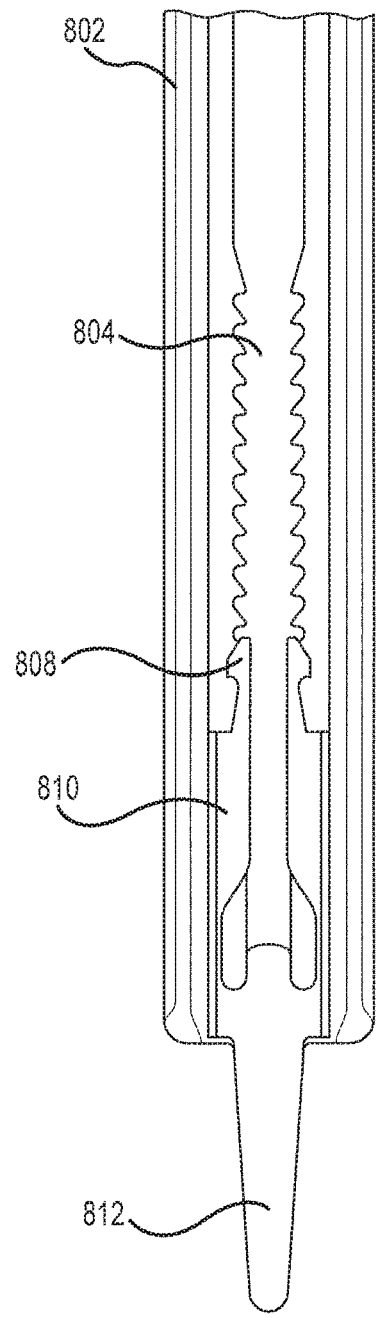
Figures 8C, 8D:
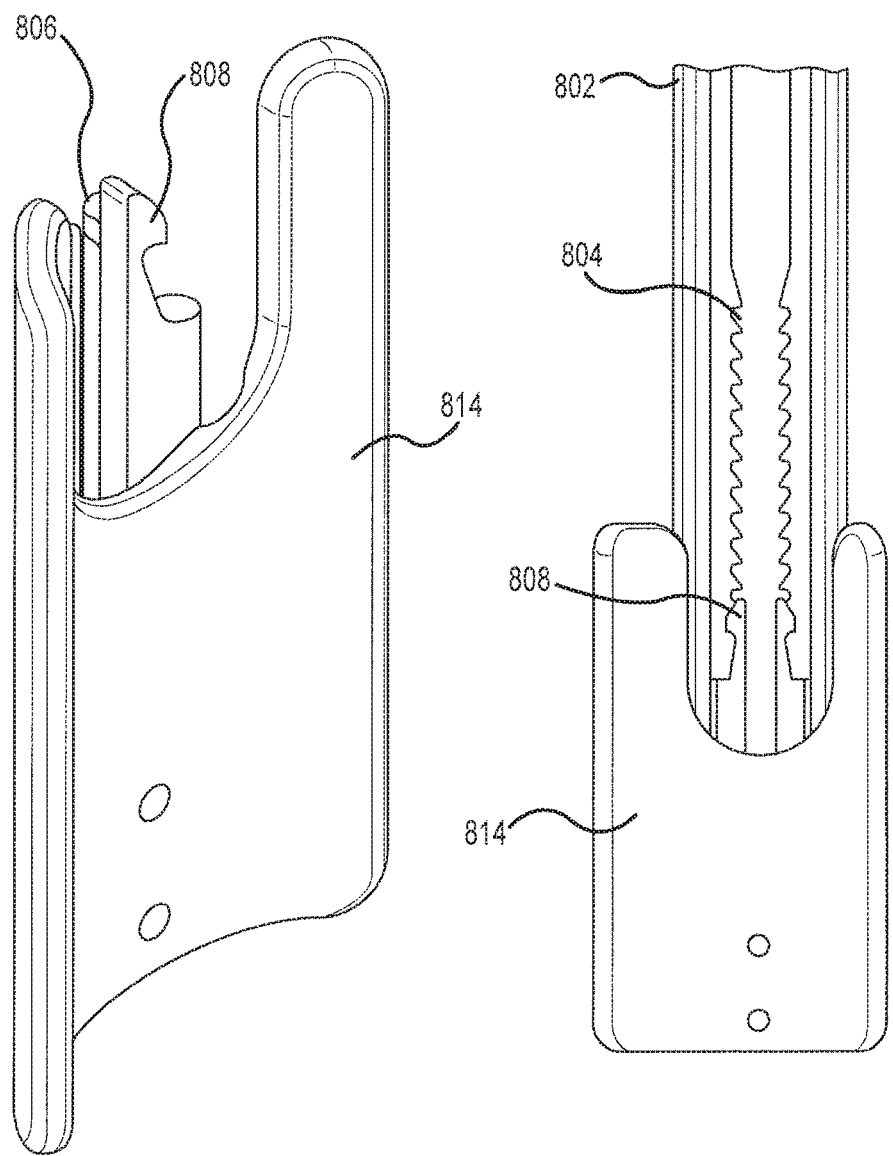
FIGS. 8C and 8D depict a perspective view of a widening shim, and the widening shim connected to a blade, respectively.
Figures 8E, 8F:
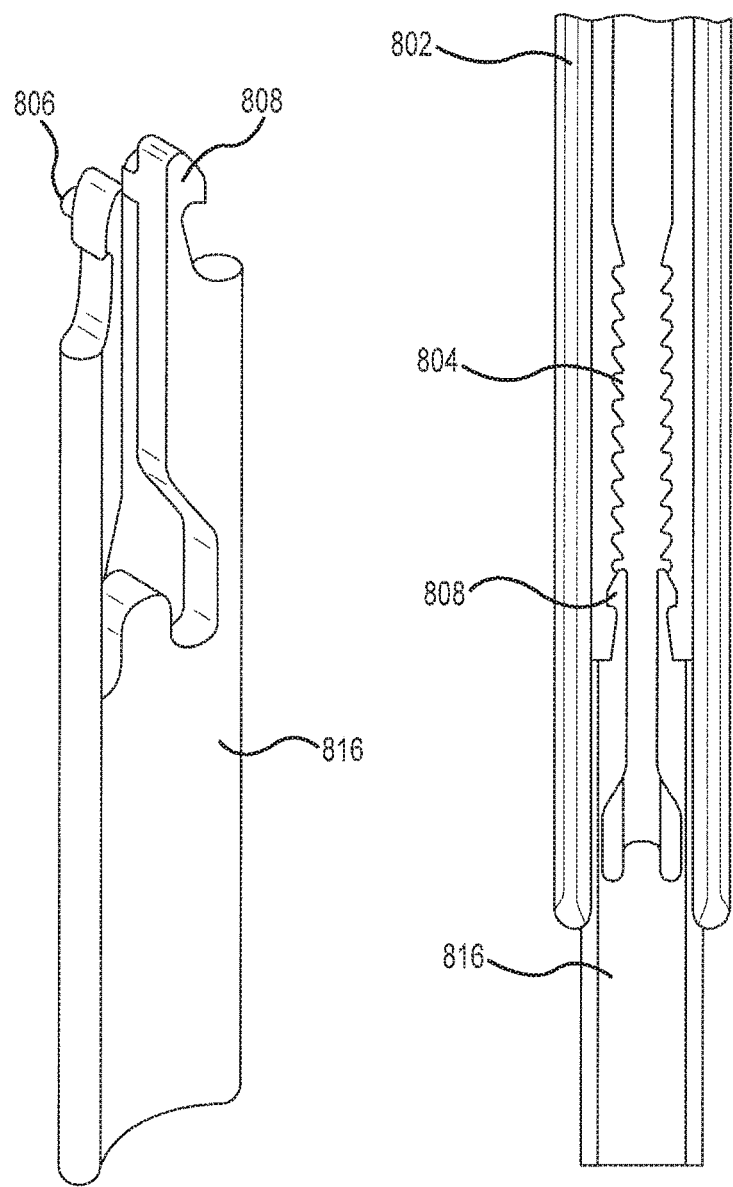
FIGS. 8E and 8F depict a perspective view of a lengthening shim, and the lengthening shim connected to a blade, respectively.

FIGS. 8A-8F depict various embodiments of shims that may be used in conjunction with a retractor device such as described herein. In the depicted embodiments, some of the shims include one or more tabs 806 or other mechanisms to engage a ratcheted groove 804 located on the interior face of the blades 802. The tab/ratchet interface allows the depth of insertion of the shim to be adjusted based on the needs of the surgeon performing the particular procedure, and the groove 804 is configured such that multiple depths may be achieved. In the depicted embodiment, the groove 804 comprises two opposing ratcheted surfaces that are engaged by opposing tabs 806 on the shim which is, in this case, an intradiscal shim 810. In some embodiments, tabs 806 extend from flexible arms 808 that may be deflected inward, such as by an elongate instrument used for shim insertion or retraction. Tab 806 is disengaged from the groove 804, allowing the shim 810 to be moved upward or downward along the blade 802. In some embodiments, arms 808 are compressed towards each other to allow shim 810 to slidingly engage the blade 802 without a ratcheting of tabs 806 and groove 804. The outer edges of shiny 810 may engage a corresponding feature in blade 802 to allow a sliding or telescoping movement between shim 810 and blade 802. In some embodiments, one or more outer edges of shim 810 engage a slot, a groove, a lip, an overhang, or the like in blade 802 to provide for a controlled sliding movement of shim 810 relative to blade 802. In this manner, the shim 810 may be adjusted to a desired position relative to blade 802, and then released to securely lock in place using tabs 806 and groove 804. This arrangement also helps prevent the shim 810 from disengaging from blade 802. The depicted intradiscal shim 810 may be used to fix a position of one of the blades 802 (typically, the posterior blade) relative to a spine. The distal tip 812 of the intradiscal shim 810 is sized and configured so as to be temporarily lodged between two vertebrae during a spinal procedure. The intradiscal shim 810 may, for example, restrict lateral movement of the blade 802 to which the shim 810 is attached. Intradiscal shim 810 also helps restrict blade 802 movement in the cranial-caudal directions, and the anterior-posterior directions as well. A widening shim 814 is depicted in FIGS. 8C and 8D and is used, inter alia, to prevent tissue creep into the spaces between the blades 802 when they are opened. A lengthening shim 816 is depicted in FIGS. 8E and 8F is used to lengthen the effective depth of penetration of the blades 802, allowing a deeper surgical corridor to be opened in a body tissue. In general, the widening and lengthening shim 814, 816 are utilized on the cranial and caudal blades. In some embodiments, the shims 810, 814, 816 are interchangeable, with each available for use with any of the retractor blades 802.

While the widening shim 814 and lengthening shim 816 are each depicted as discrete from the blades 802, in alternative embodiments hey may be non-removably coupled to the blades 802 prior to insertion into the body tissue. In a particular embodiment, intradiscal shim 810 is slidably and non-removably coupled to the posterior blade. This helps prevent the shim 810 from inadvertently disconnecting from the blade 802, which would defeat the purpose of using an intradiscal shim 810 to fix the position of the blade 802 in the body. In this manner, the intradiscal shim 810 operates as an extension of the retractor blade 802 when a distal tip 812 of the shim 810 is positioned to extend beyond the distal tip of the retractor blade 802. When not in use, the shim 810 is withdrawn into the retractor blade 802 such that the distal tip 812 of the shim 810 does not extend beyond the distal tip of the retractor blade 802.

Figure 8G:
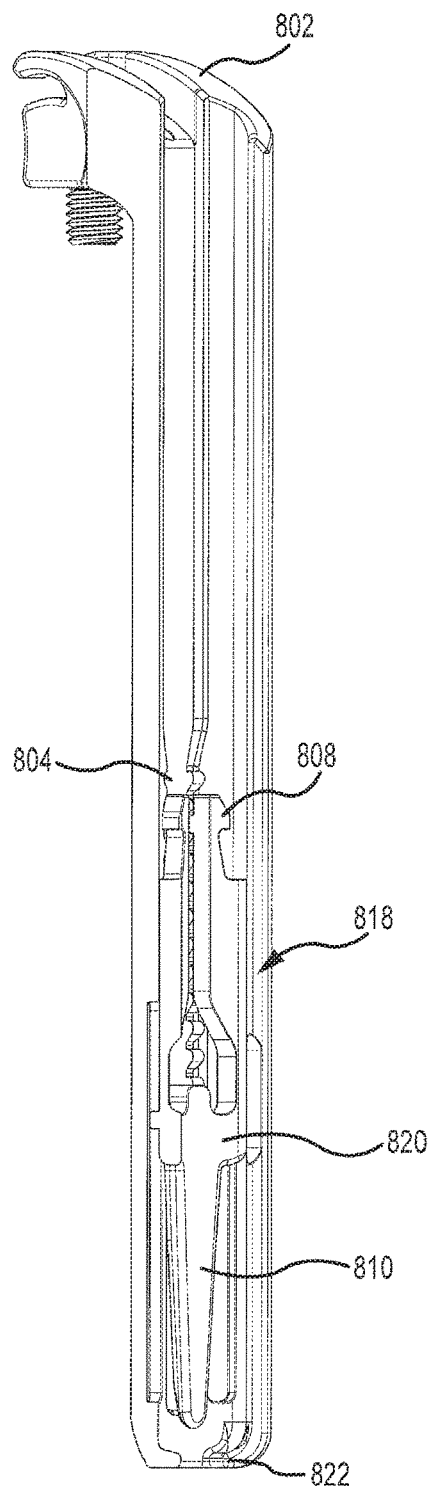
FIG. 8G depicts a sectional view of the intradiscal shim and blade of FIG. 8B.

A configuration of such a blade/shim interface where the shim is not removable from the blade 802 is depicted in FIG. 8G. The shim 810 and blade 802 are coupled together in a manner to allow a slidable relationship between the shim 810 and the blade 802. In the depicted embodiment, inner edges 818 of the blade 802 substantially surround wings 820 of the shim 810, which prevents the shim 810 from being pulled away from the blade 802. A travel stop 822 is located at a bottom of the blade groove 804 or adjacent the blade groove 804. The travel stop 822 prevents the shim 810 from being removed from the bottom of blade 802. In addition, pins or other structure (not seen in FIG. 8G) operate to restrict movement of shim 810 towards the top of blade 802. In this manner, intradiscal shim 810 has a limited range of sliding motion relative to blade 802, but is not removable from blade 802 through either the top (proximal) or bottom (distal) ends of blade 802.

Figures 8H, 8I:
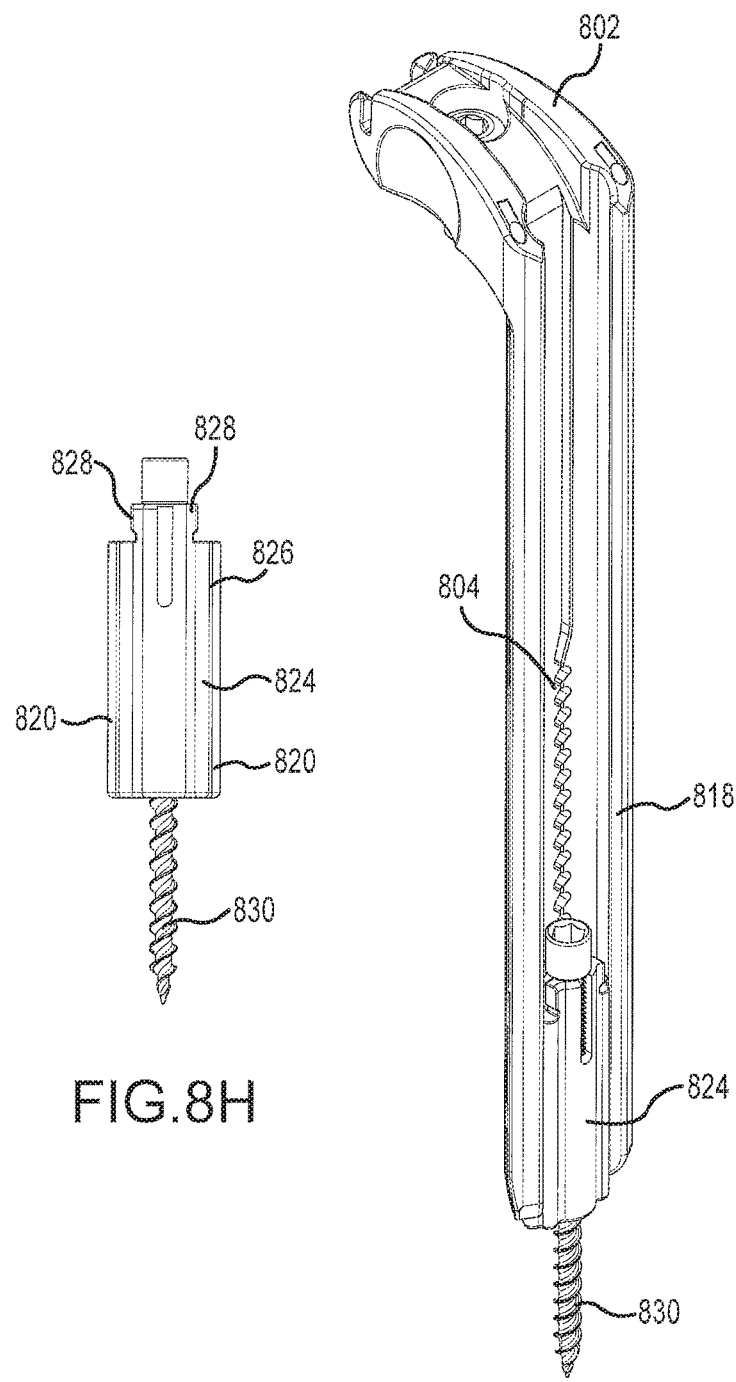
FIGS. 8H and 8I depict a perspective view of a first anchoring shim, and the first anchoring shim connected to a blade, respectively.

FIGS. 8H and 8I depict an anchoring shim 824 that may be used with the retractor devices described herein. The anchoring shim 824 includes a body 826 that is configured to slide within the groove 804 of the blade 802. The blade 802 includes inner edges 818 that substantially surround or engage wings 820 of the anchoring shim 824, similar to the blades and wings depicted in FIG. 8G, above. Unlike the shims of FIGS. 8A-8G, however, the anchoring shim 824 lacks any rear projections to engage with the ratcheted groove 804. Instead, the anchoring shim 824 is configured to slide unimpeded along the blade 802. Tabs 828 may engage with an elongate tool to move the anchoring shim 824 within the groove 804 or to hold the shim 824 steady. Unlike the tabs 806 depicted above, however, these tabs 828 need not be deflected inward to move the shim 824. Instead, the tabs 828 serve as a point of connection with the elongate tool. In some embodiments, the elongate tool also engages the blade inner edges, wings, grooves, or similar structure of the blade for additional control of shim movements when using the elongate tool. Extending from and through the body 826 is a fastener 830 that may be used to anchor the blade 802 to a vertebral body. In the depicted embodiment, fastener 830 is a threaded screw with a tool engaging proximal portion. Other fasteners also may be used, including pins, elongate wires, or the like. In sonic embodiments, the anchoring shim 824 is utilized on the cranial or caudal blades, for coupling of the fastener 830 to a vertebral body. A head of the fastener 830 may be actuated by a tool, such as a hex driver or other device for securing the fastener 830 to bone. Once one of either the cranial or caudal blades are anchored via the shim 824, opening of the retractor device arms will result in the unanchored blade moving away from the anchored blade, thus moving a central axis of the surgical corridor away from the anchored blade.

Figures 8J, 8K:
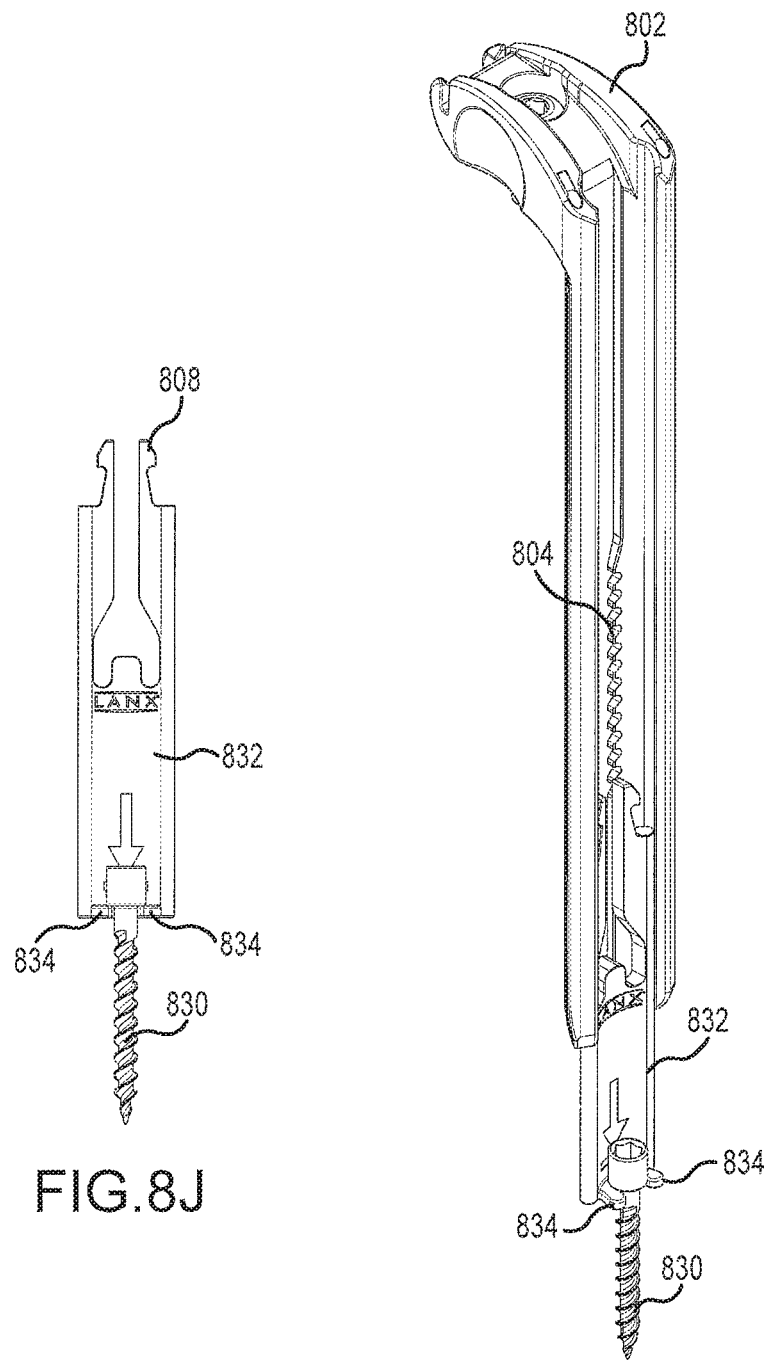
FIGS. 8J and 8K depict a perspective view of a second anchoring shim, and the second anchoring shim connected to a blade, respectively.

FIGS. 8J and 8K depict another embodiment of an anchoring shim 832. This anchoring shim 832 utilizes deflectable tabs 808 to selectively locate associated projections (not shown) within the ratcheted groove 804 (similar to the shims of FIGS. 8A-8G). Two fastener retention ears 834 are located on either side of the vertebral screw 830. This anchoring shim 832 differs additionally from the anchoring shire 824 of FIGS. 8H and 8I in that the fastener holding force provided by the retention ears 834 is less than that provided by the enclosed body 824 of the first anchoring shim 824 of FIGS. 8H and 8I. For example, the shim 832 main body and ears 834 generally surround fastener 830 on three sides, leaving a gap on one side. As a result, a force applied to blade 802 in a direction generally opposite this gap may allow shim 832 to disengage from fastener 830. In some circumstances, this may be desired. In other cases, the anchoring shim 832 may be used when the blades 802 have already been opened.

Figures 8L, 8M:
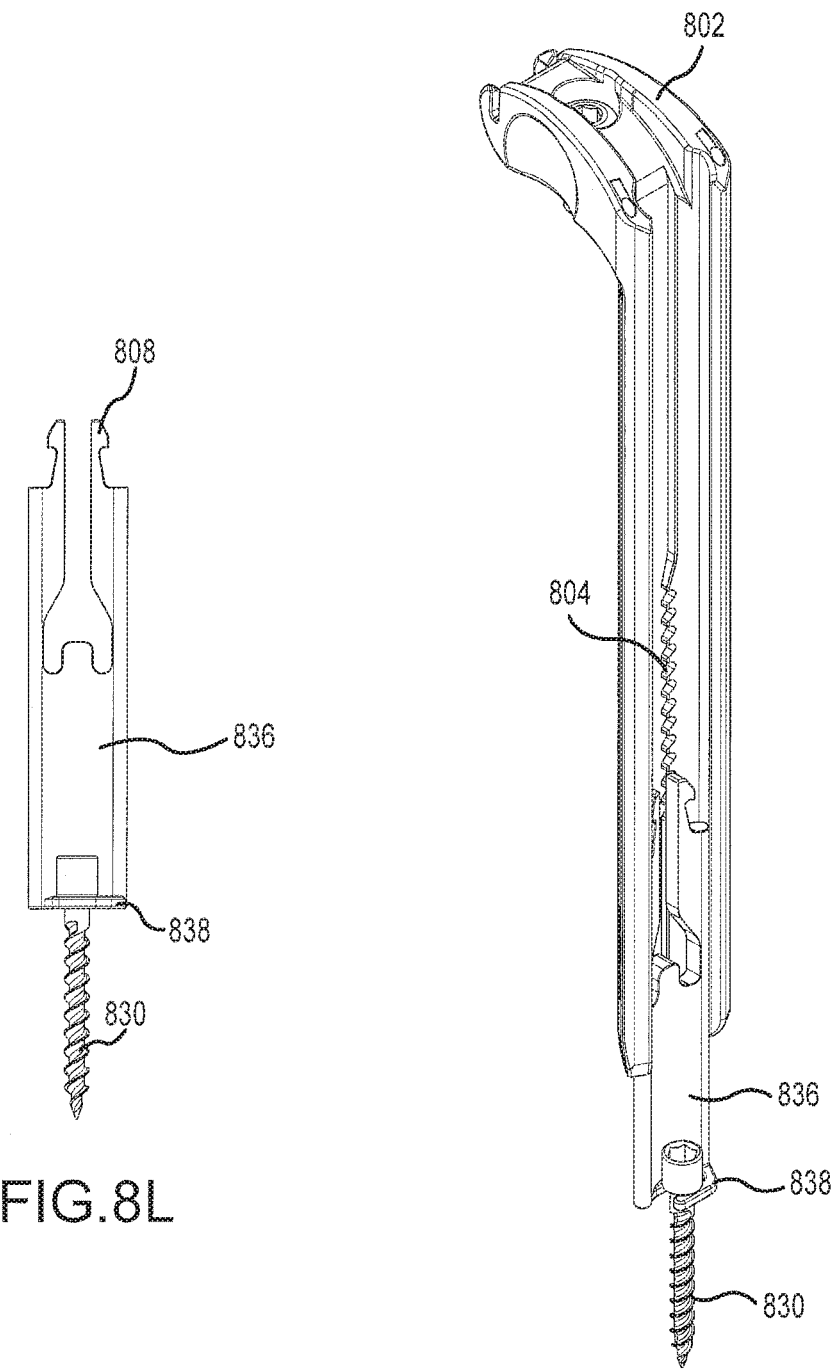
FIGS. 8L and 8M depict a perspective view of a third anchoring shim, and the third anchoring shim connected to a blade, respectively.

FIGS. 8L and 8M depict yet another embodiment of an anchoring shim 836, that also utilizes deflectable tabs 808 to selectively locate associated projections (not shown) within the ratcheted groove 804 (similar to the shims of FIGS. 8A-8G). A single fastener retention hook 838 wraps at least partially around the fastener 830. Accordingly, this anchoring shim 836 may provide more screw holding force than the embodiment depicted in FIGS. 8J and 8K. Regardless of the differences, use of each of the anchoring shims described herein nay be desirable at different stages of a surgical procedure, depending on particular working conditions, clearance issues, or surgeon preferences.

Figure 8N:
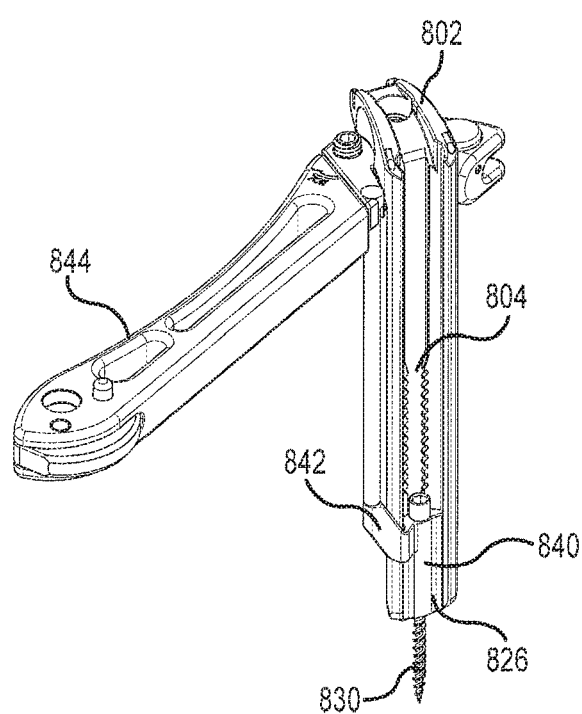
FIG. 8N depicts a perspective view of a fourth anchoring shim connected to a blade.

Yet another anchoring shim 840 is depicted in FIG. 8N. This anchoring shim 840 is similar in configuration to the anchoring shim 824 of FIGS. 8H and 8I, in that it may freely slide within the groove 804 of the blade 802, Further, housing 826 has a channel or hole there through to receive the fastener 830. Again, fastener 830 may be a threaded screw, a non-threaded screw, a pin, an elongate wire, or the like. Connected to the housing 826 is an elongate arm 842. Arm 842 is coupled to the armature 844 to which the blade 802 is attached. In this manner, once the fastener 830 is anchored to the vertebral body, the blade 802 may be disconnected from the arm 844 and from the shim 840 and removed from the surgical corridor. This may occur, for example, by removing screw 612 holding the proximal end of blade 802 to armature 844, and lifting the blade 802 vertically to disengage blade 802 from shim 840. The elongate arm 842 allows the armature 844, and thus the retractor, to remain secured to the anchoring shim 840. Accordingly, access to the interior of the surgical corridor may be improved with the blade 802 removed therefrom.

In another embodiment, one or more of the retractor blades comprise telescoping blades. In such an embodiment, the retractor blade includes a proximal-most portion coupled to the retractor arm and a distal-most portion. The proximal-most portion and the distal-most portion overlap in a telescoping or nestled fashion to allow the retractor blade to have a variable overall length. In some embodiments, the telescoping blade components have a slidable relationship, but are non-separable, to ensure they stay connected while opening or holding the surgical corridor. In some embodiments, shims described herein have a boss, peg, or similar feature on the back of the shim which slides in a groove or slot in the blade to which it is coupled. The groove has a closed distal end that operates as a travel stop for the shim boss or the like. In this manner, the boss and groove combination, or similar structure, prevents the shim from sliding out the distal end of the blade.

Figure 9A:
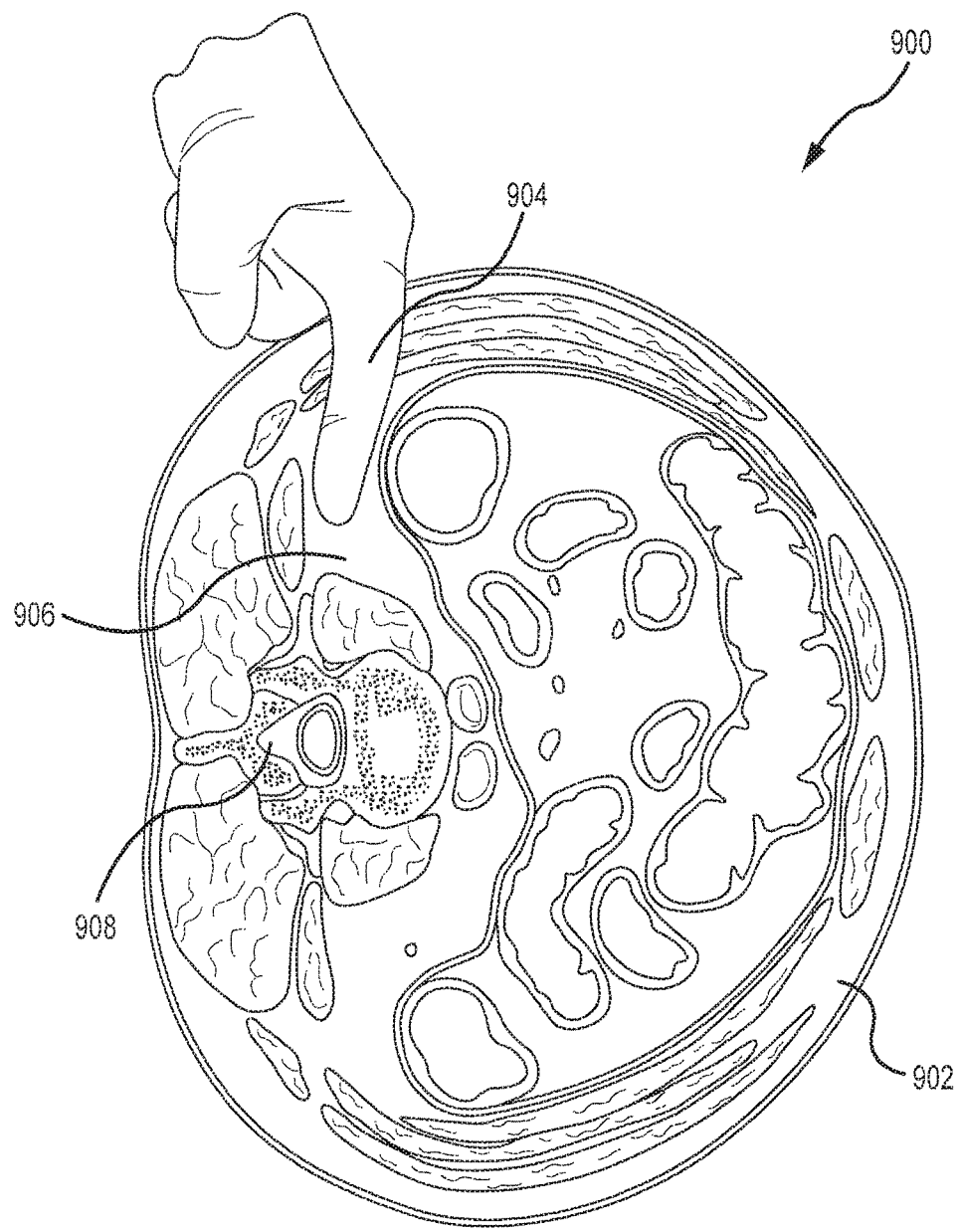
FIGS. 9A-9F depict a method of using a retractor system for a lateral spinal surgical procedure.
Figure 9B:
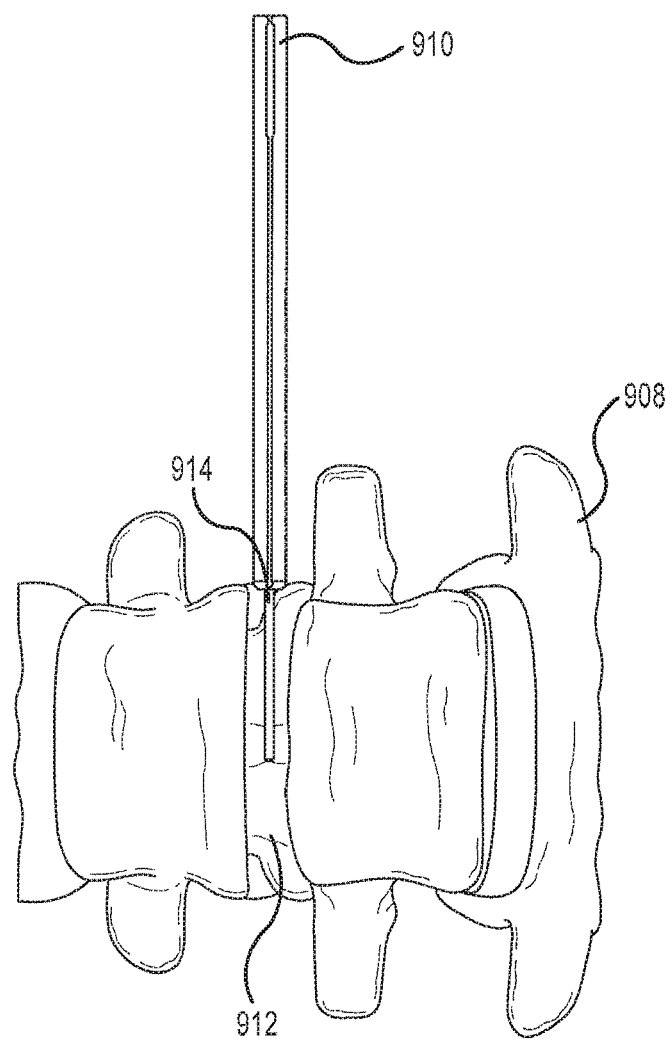
Figure 9C:
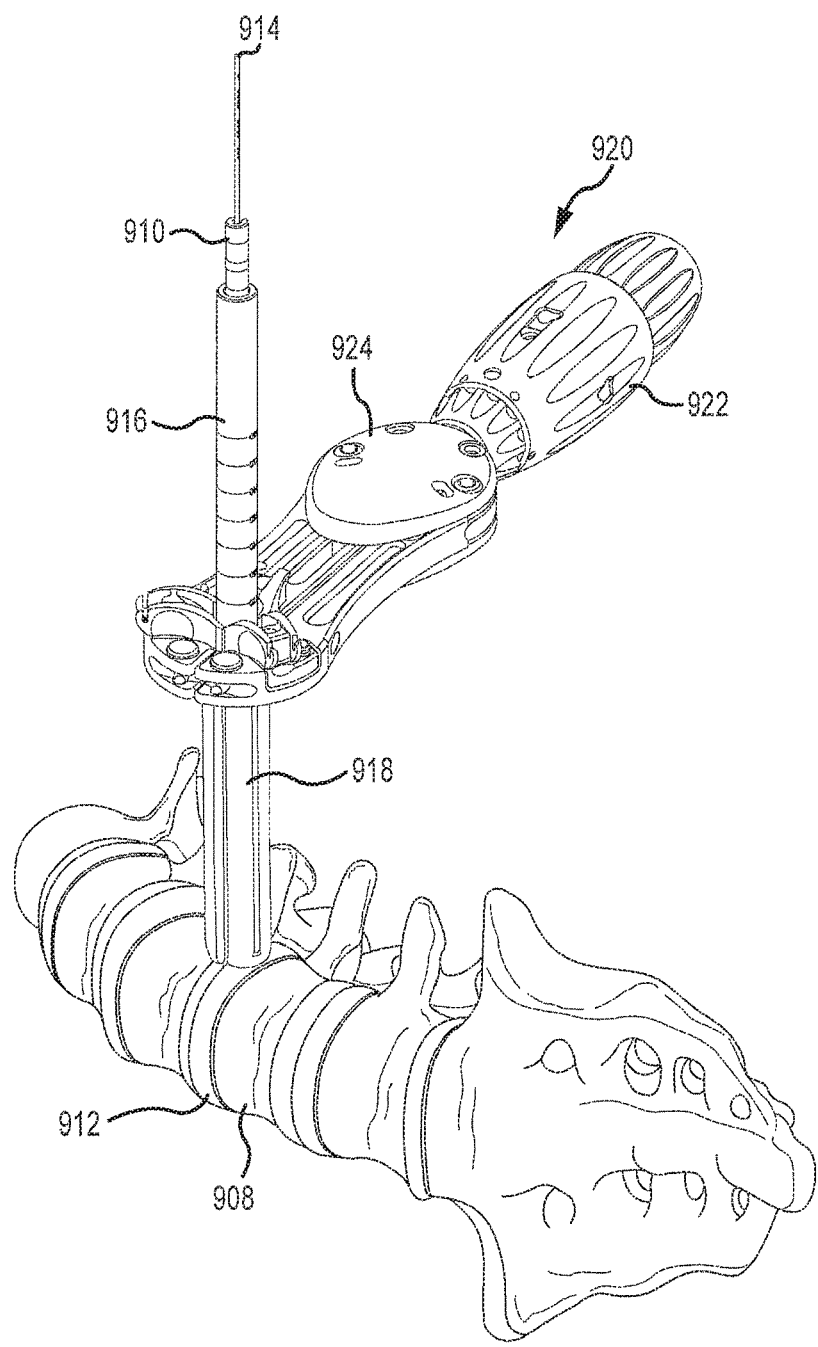

FIGS. 9A-9C depict a method of performing a surgical procedure with the systems and devices described herein. FIG. 9A depicts a transverse cross-sectional view 900 of the torso 902 of a human body. For a lateral surgical procedure, the patient is positioned on a surgical table and x-rays, such as true lateral and anterior-posterior, may be taken. The surgeon may then make a first incision in the desired location. The initial distraction corridor (i.e., separation of the muscle fibers) is made using blunt dissection, as depicted in FIG. 9A. Blunt dissection requires a surgeon to digitally penetrate the torso 902 with one or more fingers 904. Using blunt dissection, a posteriorly-directed trajectory (aiming for the transverse process) is used to enter the retroperitoneal space 906. Once the retroperitoneal space 906 has been entered, the tissue is distracted into the free space of the retroperitoneum. The peritoneum may be moved anterior with the fingers 904 and blunt dissection continued to palpate to the transverse process posteriorly. The finger 904 may be slid forward to the retro-psoas recess and over the dome of the psoas to ensure retroperitoneal viscera have been safely retracted anteriorly. In general, the distraction corridor is formed in a direction generally towards the spine 908.

FIG. 9B depicts an anterior view of a spine 908. After the blunt dissection depicted in FIG. 9A, a first dilator 910 is inserted through the incision. The location of the first dilator 910 may be verified using lateral fluoroscopy. It is desirable that the first dilator 910 be targeted to the center of the intervertebral disc space 912. The first dilator 910 may be advanced through the psoas muscle (not shown) using a rotating motion. In some cases, the first dilator 910 may be located between about the center and about the posterior-third of the disc space 912, and the position verified using lateral fluoroscopy. Once the first dilator 910 is an acceptable position, a K-wire 914 may be inserted through the center thereof and into the disc space 912. The K-wire 914 may be inserted approximately half-way across the disc space 912 to assist in securing the access entry point. Again, anterior-posterior and lateral fluoroscopy may be used to ensure the proper location of the K-wire 914 and the first dilator 910. Thereafter, a second dilator (not shown in FIG. 9B) may be advanced over the first dilator 910, using a rotating motion.

FIG. 9C depicts a perspective view of a spine 908. After insertion of the second dilator 916 over the first dilator 910, the retractor blades 918 of the retractor device 920 are placed around the second dilator 916 and advanced downward into position. Position of the blades 918 may be verified as in-line with the disc space using fluoroscopy. It is generally desirable that the retractor 920 be parallel to the disc space 912 and the retractor working channel (the space between the blades 918) be aligned with the disc space 912. In some cases, such as when working around other bony structure (e.g., ribs, iliac crest, etc), the retractor 920 may be angled in the cranial/caudal direction relative to the patient. The retractor 920 may next be secured in place by connecting an articulating arm (not shown) to one of the retractor connection points. The articulating arm is also connected to a generally fixed or stable structure, such as the surgical table, to provide a steady platform for retractor 920.

The surgical corridor may now be expanded and otherwise altered as desired in accordance with the manipulations of the retractor device 920 described above. Typical functions include separation of the cranial/caudal blades, retraction of the posterior blade, toeing of the blades, etc. Once the retractor blades 918 are opened to the desired position, the first dilator 910, the second dilator 916, and the K-wire 914 may be removed. Once these components are removed, an implant insertion procedure may be performed. Any number of actions may be taken, in almost any order, to insert an implant. For example, an intradiscal shim (as depicted above), may be extended out of the posterior blade in which it is located during insertion and into the disc space 912. The position of this element may be verified using anterior-posterior fluoroscopy. Additionally, widening or lengthening shims may be advanced as needed. If desired, the handle 922 may be removed from the retractor device 920. Annulotomy and discectomy procedures may then be undertaken to remove the disc material, and an appropriately sized implant may be inserted. After implantation, the retractor blades 918 may be closed and removed from the body and the surgical corridor sutured closed.

Figure 9D:
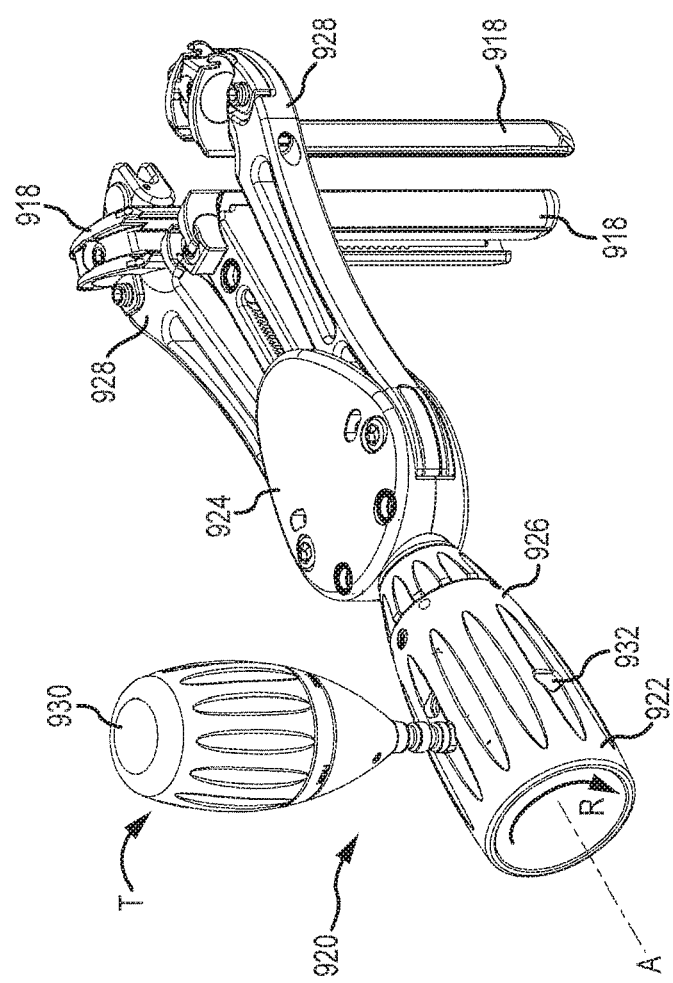

FIG. 9D depicts a perspective view of the retractor device 920 with the blades 918 in an open position. In this figure, the spine has been removed for clarity. As described elsewhere herein, rotation R of the main actuator 926 of the handle 922 opens the cranial and caudal arms 928. Resistance of the patient tissue, however, may make difficult the rotation R of the main actuator 926 about the handle axis A. In that case, the posterior actuator 930 may be withdrawn from the handle 922 along the axis A. Thereafter, a tip of the posterior actuator 930 may be inserted into one of several torque points 932 about an outer diameter of the main actuator 926. A torque T may be applied to the posterior actuator 930, such that actuator 930t acts as a lever to make for easier rotation R of the main actuator 926. Once the arms 928 have been opened to the desired position, the posterior actuator 930 may be returned to its original location on the handle 922. As previously described, in some embodiments main actuator 926 operates a worm gear drive to allow blades 918 to be opened a desired amount and maintained.

Figure 9E:
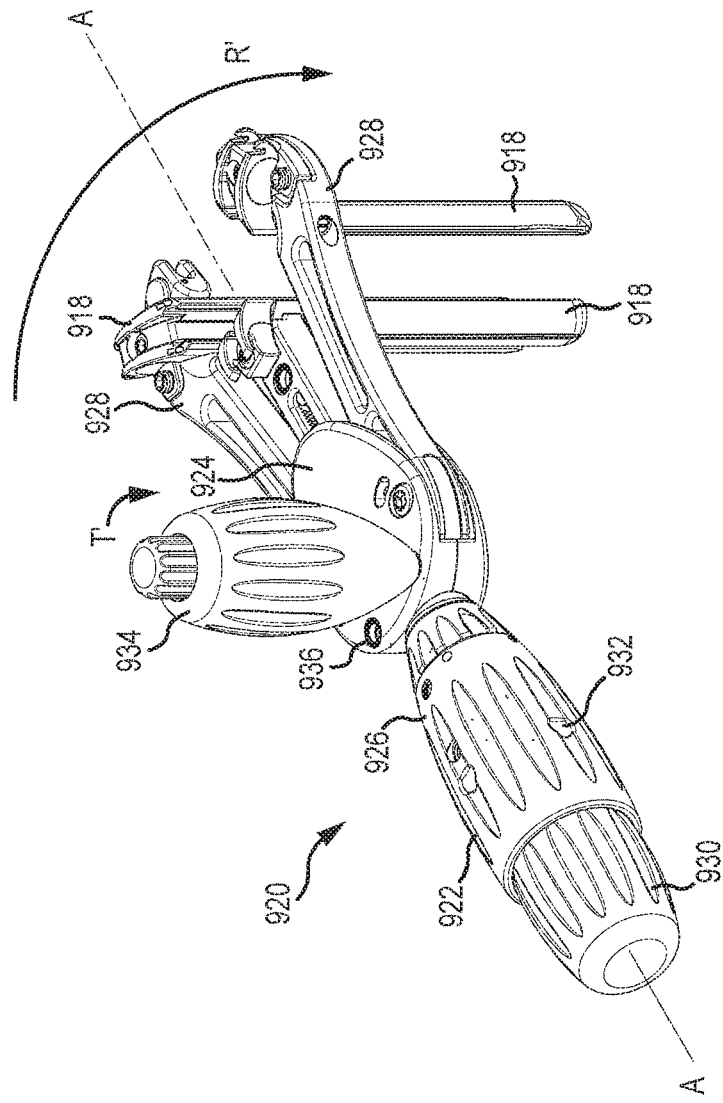

FIG. 9E depicts a perspective view of the retractor device 920 with the blades 918 in an open position. In this figure, the spine has been removed for clarity. Forces acting on the blades 918 by the body tissue may also cause the retractor device 920 to move undesirably. To overcome such forces, a pivot lever 934 may be connected to one of the arm connections 936 (that are typically used for connection to an articulating arm, as described above) and a torque T' applied. This will rotate R' the entire device 920 about the device axis A, thus improving the ability to position the device 920 as desired. This may be especially helpful when attempting to anchor any of the blades 918 to the vertebrae with the anchoring shims described above. Pivot lever 934 also may be used to rotate retractor 920 about the dilators to aid in the insertion of retractor 920 towards the surgical site, or provide a hand-hold for a user to better hold, support or manipulate retractor 920.

Figure 9F:
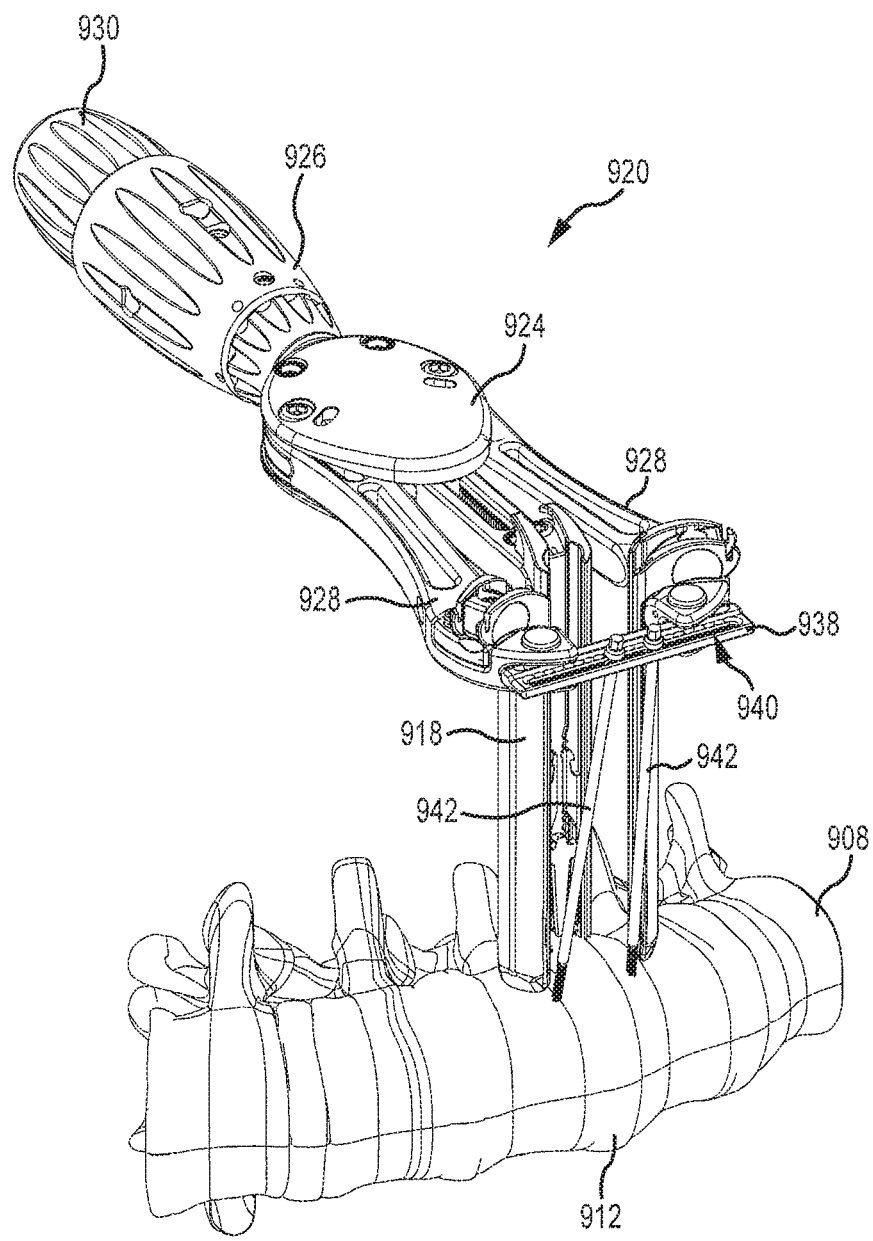

FIG. 9F depicts other components that may be utilized with the retractor device 920 to fix the position of the device 920 within the body and/or to create or maintain a desired operative opening. As shown, a span member 938 connects to the free ends of both of the articulating arms 928. In some embodiments, the span 938 defines a slot 940 through which one or more anchor rods 942 may be passed. The anchor rods 942 may be screwed into vertebral bodies, typically on either side of a target disc 912. In addition to fixing the position of the device 920 relative to the spine 908, the anchor rods 942 may also be used to hold back tissue that may creep into the space between the cranial and caudal blades 918 once opened.

Figure 9G:
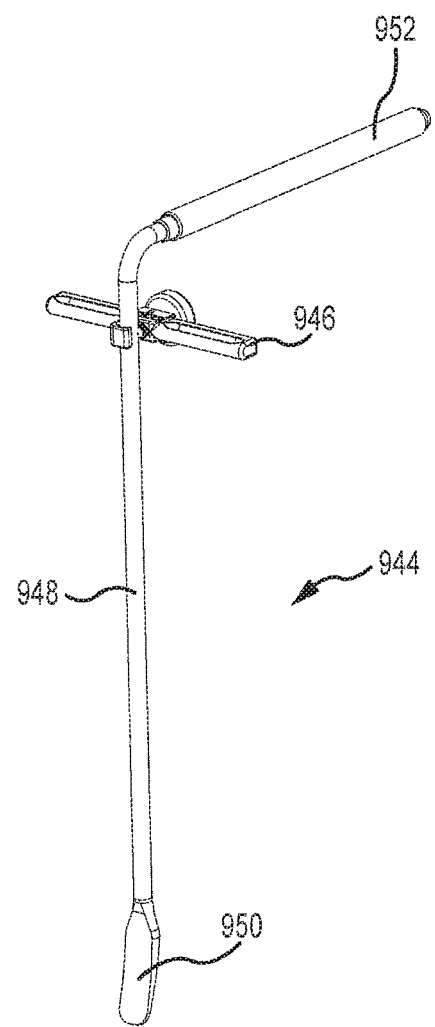
FIG. 9G depicts a paddle for use with a retractor system.

In an alternative embodiment, an additional or optional paddle 944 is provided to help create or maintain a desired operative window. For example, and as depicted in FIG. 9G, paddle 944 may be coupled to a span 946 placed between the two pivoting arms (not depicted in FIG. 9G) after the surgical access corridor is created. The span 946 may be similar or identical to the span 938 of FIG, 9F. In general, the paddle 944 is positioned generally opposite the posterior blade, although it could be coupled to the span 938 at any location. In this manner, the paddle 946 helps maintain an additional side, such as an anterior side, of the surgical access corridor. The paddle may simply be a static blade or rod, or other elongate member having any cross-sectional profile. In the depicted embodiment, the paddle 944 includes an elongate rod 948 having a wider base 950. Opposite the wider base 950 is a handle 952 that may be moved as desired to position the paddle 944. A fastener member, shown as a threaded knob, operates to couple elongate rod 948 to the span 946. The fastener member further may couple the elongate rod 948 to control the depth of paddle 944 relative to the surgical location. In most embodiments, the paddle 944 lacks any additional structure that would enable use thereof with shims. However, in alternative embodiments, such structure (grooves, etc.) may be incorporated if desired. Since the paddle 944 is generally used to prevent tissue creep from the space between the cranial and caudal blades, any type of rigid structure that can hold tissue is sufficient.

The methods depicted in FIGS. 9A-9C may be modified by the incorporation of known neuromonitoring techniques. Neuromonitoring is not required to perform the procedures described herein, but may be desirable and is therefore incorporated at the surgeon's discretion. A number of different neuromonitoring systems may be utilized. Manufacturers of acceptable systems include Caldwell Laboratories, Inc., of Kennewick, Wash. Caldwell Laboratories, as well as other manufacturers, also manufactures monitoring probes (also referred to as electrodes) that may be utilized in conjunction with various surgical instruments or alone for treatment or diagnostic purposes. These electrodes are typically disposable elements that may be inserted into the body as required. The dilators described herein, as well as the retractor blades, include one or more channels to receive such probes. The probes may be inserted before or after insertion of the particular component into the body, again at the surgeon's discretion. Neuromonitoring techniques, in conjunction or discrete from surgical implements, are well-known to persons of skill in the art. Regardless, when electrodes are used in conjunction with the components described herein, the electrode is typically first inserted into the appropriate channel of the component. Once the component is inserted into the desired depth within the body, the neuromonitoring equipment is then activated and the response from the nerves detected. Proper operation of neuromonitoring equipment typically requires that the component first be inserted, stopped at a desired position, then neuromonitoring performed. This gives the surgeon the feedback necessary to adjust the position of the component so as to avoid the nerves. This may be performed in steps, advancing the component a certain distance, stopping advancement, monitoring, and repeating advancement as required.

Figure 10A:
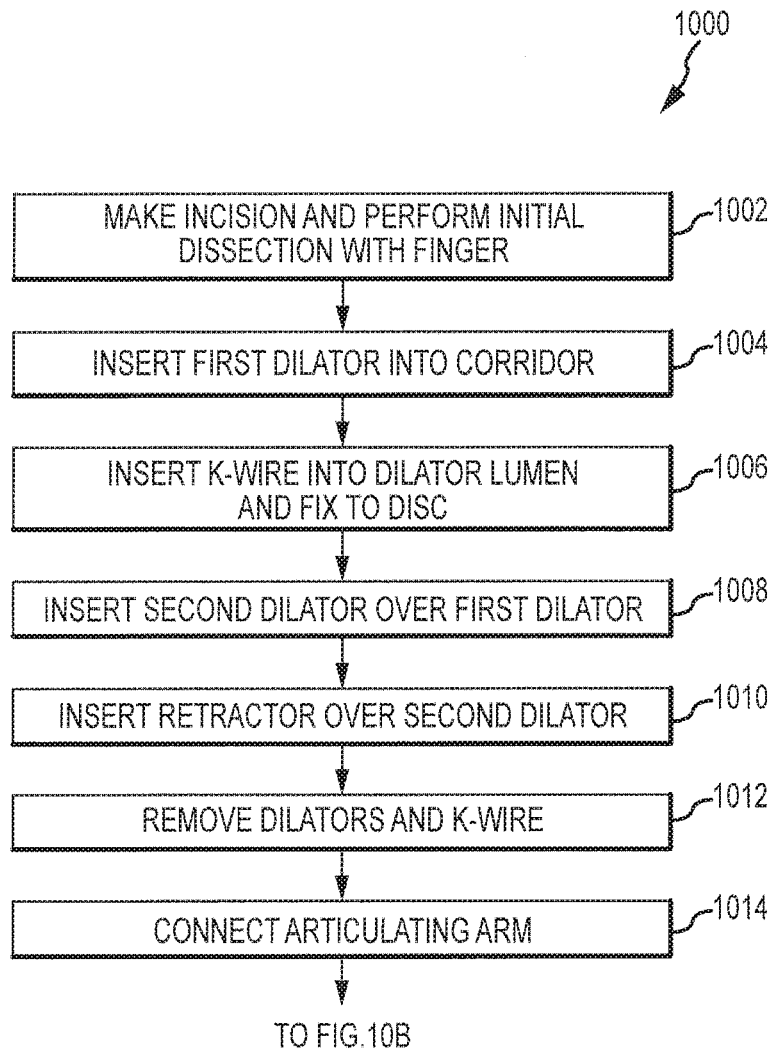
FIGS. 10A and 10B depict a method of using a retractor system.
Figure 10B:
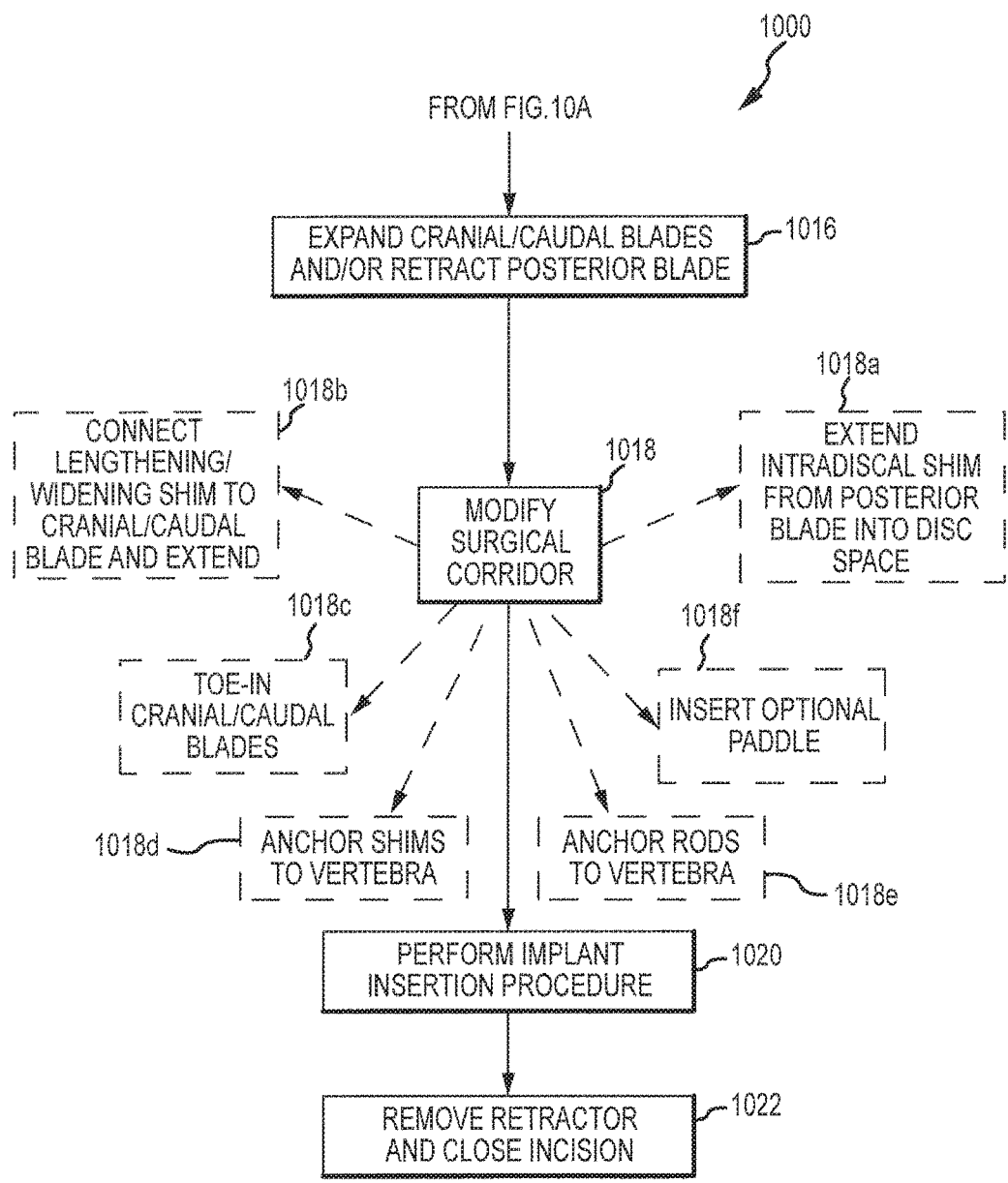

FIGS. 10A and 10B depict a method 1000 of using a retractor system. Although the method is described in the context of lateral-approach spinal surgery, it should be noted that the systems and methods described herein may be used in virtually any surgery where limited muscular trauma is desired. In surgeries where limited, controlled separation of muscle fibers is desirable, the retractor system described herein may be particularly advantageous. Although described in conjunction with FIGS. 10A and 10B, the order of steps or procedures may differ from that depicted. First, as previously depicted in FIG. 9A, the patient is properly positioned and an incision is made in the desired location and the initial distraction corridor is formed via blunt (i.e., digital) dissection (operation 1002). After the initial distraction corridor is formed, a first dilator is inserted (operation 1004). Thereafter, a K-wire may be inserted via the lumen of the first dilator and secured to the disc space (operation 1006). This helps prevent movement of the dilator, thus keeping that element (and the subsequent elements) properly positioned within the body. Thereafter, a second dilator is inserted over the first dilator (operation 1008), such that the first dilator (and K-wire located therein) are located within the lumen of the second dilator. If desired, additional dilators may be used to create a larger corridor before insertion of the retractor. A retractor device is then inserted over the second dilator (operation 1010). During insertion of the retractor device, the arms and blades of the device are in the closed position (that is, the position where each blade is located as close as possible to the two adjacent blades). Blades containing the intradiscal shim have a sufficiently low profile to allow for insertion of the retractor with the intradiscal shim. Further, the low profile of the intradiscal shim and the shim extension tool allows the shim to be advanced from a retracted position to an extended position after the retractor has been inserted and before the dilators have been removed. This helps secure the retractor with the intradiscal shim between two bony structures, such as vertebrae, before the dilator(s) and/or K wire is removed. Additionally, any blades that may have toeing functionality should be set such that the blades are parallel to the direction of insertion. During insertion, all three of the blades of the retractor device are inserted simultaneously.

Once the retractor device is inserted to the desired depth, the K-wire and dilators may be removed from the area between the blades (operation 1012). To secure the retractor device at the desired location, an articulating arm connected to the surgical table or other fixed element may be connected to one of the connection points on the retractor device body or posterior arm (operation 1014). In some embodiments, operation 1014 occurs prior to operation 1012. In addition to the articulating arm, an intradiscal shim located within the posterior blade may also be extended into the disc space to further secure the device in the desired location. The operation of extending the intradiscal shim is described below. Once the retractor device is in the desired position, the cranial and caudal arms (and, therefore the cranial/caudal blades) may be expanded and the posterior blade retracted (operation 1016). Once the various blades are expanded to the desired distance, a surgical procedure may be performed.

However, the retractor device described herein includes, or may be utilized with, a number of supplemental components to increase versatility of the device. This versatility allows a surgeon to modify the surgical corridor (operation 1018) as required or desired to address particular internal anatomical conditions, or to otherwise improve usability of the retractor device. For example, and as noted first above, the intradiscal shim may be extended from its stored position in the posterior blade to further fix the position of the device relative to the spine (operation 1018a). Other shims may also be used in conjunction with the cranial and caudal blades. For example, the widening and/or lengthening shim may be used to supplement the blades. In some embodiments, the shims are loaded into their respective blades after the retractor blades have been inserted into the patient. This occurs, for example, by inserting the shim down through the proximal end (top) of the blade using a shim inserter tool. Alternatively, at least some of the shims have a sufficiently low profile to be inserted into the blades prior to insertion of the blades into the patient. As previously noted, there may be a small gap between one or more blades as the blades are inserted over the largest dilator. To use either of the widening or lengthening shims, the shim is placed into the shim groove in the desired blade, then advanced down towards the end of the blade (operation 1018b). The tab and groove interface of the shim and blade allows the shim to be advanced as far as required or desired, and resists or prevents undesired movement of the shim back towards the proximal end of the blade. The cranial and caudal blades may also be toed out to increase the area of the corridor proximate the spine (operation 1018c). If more robust fixation of the blades within the surgical corridor is desired, anchoring shims may be used to engage the vertebra (operation 1018d). Typically, the anchoring shims are inserted after the blades have been inserted into the patient and opened or separated at least enough to allow shim insertion. Alternatively or additionally, one or more rods may also be anchored (operation 1018e). Another modification of the corridor includes utilizing the supplemental paddle between the cranial and caudal arms to prevent tissue creep into the space therebetween (operation 1018f). Of course, any or all of these operations may be performed at any desired time to modify, enhance, or otherwise support the surgical corridor.

Regardless, once the desired corridor is obtained, an implant insertion procedure is performed (operation 1020). The steps of the implant insertion procedure would be known to a person of skill in the art and are not described further. Once the implant insertion procedure is completed, shims and other optional features are retracted or removed. The retractor blades may be closed and the device removed from the body, allowing the surgeon to close the incision (operation 1022). As described above, neuromonitoring may be utilized during any point of the method, at the discretion of the surgeon.

Materials utilized in the manufacture of the retractor system may be those typically used in surgical equipment. Stainless steel, titanium, and other robust metals that may be sterilized may be used. In applications where fluoroscopy is desirable or required during the procedure (e.g., in the spinal surgery procedures described herein), radio-lucent materials may be particularly desirable. In those applications, aluminum, anodized aluminum, and rigid polymers may be utilized. In some embodiments, the retractor blades comprise aluminum which has been anodized with a hard coat anodizing process to create an electrical insulated material. Such blades may be useful, for example, in the event the surgeon prefers to use electrical nerve monitoring equipment. Carbon fiber-reinforced polymers may be particular useful, as they are lightweight, extremely strong, and may be sterilized. Of course, retractor systems utilizing a combination of materials may be used. For example, radio-lucent materials may be used for the blades and less expensive radio-opaque material may be utilized for the elongate element and armatures. Use of radio-lucent materials for the cover plate, armatures, and body may be particularly advantageous, as an instrument so configured will be less visible in lateral x-rays. Additionally, radio-opaque materials may be impregnated in discrete locations of components manufactured of radio-lucent materials such that position of certain parts of the system may be visible during procedures, without impeding overall visibility.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the technology. Accordingly, what is desired to be secured by Letters Patent is the technology as defined and differentiated in the following claims, and all equivalents.

What is claimed is:

1. A surgical retractor comprising:
a retractor body;
a first armature pivotably coupled to the retractor body at a first pivot point, the first armature rotatable between a first closed position and a first open position;
a second armature pivotably coupled to the retractor body at a second pivot point spaced apart from the first pivot point, the second armature rotatable between a second closed position and a second open position;
a translatable armature disposed between the first pivot point and the second pivot point, the translatable armature translatable between a third closed position and a third open position;
a first actuator coupled to the retractor body and aligned with the translatable armature;
a worm drive coupled to the first actuator, the first actuator rotatable to rotate the worm drive to operate the first armature and the second armature independent of the translatable armature; and
a second actuator coupled to the retractor body and rotatable to linearly translate the translatable armature.

2. The surgical retractor of claim 1, further comprising:
a slot; and
a pin associated the first armature, the pin engaging the slot to limit rotation of the first armature relative to the body.

3. The surgical retractor of claim 2, wherein the slot comprises an arcuate shape.

4. The surgical retractor of claim 1, further comprising:
first and second cover plates enclosing at least a portion of the worm drive.

5. The surgical retractor of claim 1, wherein one or more of the first and second actuators are removable.

6. The surgical retractor of claim 1, further comprising:
a span coupleable to distal portions of the first and second armatures.

7. The surgical retractor of claim 1, further comprising:
a first blade coupleable to a distal portion of the first armature; and
a toeing screw engageable with the first armature and operable to adjust a toe angle of the first blade.

8. The surgical retractor of claim 1, further comprising:
a first blade coupleable to a distal portion of the first armature; and
a first shim coupleable to a distal portion of the first retractor blade.

9. The surgical retractor of claim 8, wherein the first shim further comprises a pair of tabs extending from a proximal portion of the first shim; and
wherein the first blade further comprises a plurality of pairs of grooves configured to receive the pair of tabs such that the pair of tabs can lockingly engage each pair of grooves.

10. The surgical retractor of claim 9, wherein the plurality of grooves are angled to enable a ratcheting engagement between the plurality of grooves and the pair of tabs.

11. The surgical retractor of claim 1, wherein the first and second armatures, together with the translating armature form an opening sized to receive a dilator when the first armature is in the first closed position, when the second armature is in the second closed position, and when the translating armature is in the third closed position.

12. A surgical retractor comprising:
a retractor body;
a first armature coupled to the retractor body at a first pivot point, the first armature pivotable between a first closed position and a first open position;
a second armature coupled to the retractor body at a second pivot point spaced apart from the first pivot point, the second armature pivotable between a second closed position and a second open position;
a translatable armature disposed along a longitudinal axis running between the first pivot point and the second pivot point, the translatable armature translatable between a third closed position and a third open position;
a first actuator coupled to the retractor body and aligned along the longitudinal axis, the first actuator actuatable to operate the first armature and the second armature independent of the translatable armature, each of the first armature and the second armature further comprising a set of gear teeth disposed along an arcuate surface to interface with the first actuator; and
a second actuator coupled to the retractor body and actuatable to linearly translate the translatable armature.

13. The surgical retractor of claim 12, wherein the first actuator is operable to move a drive mechanism, wherein at least a portion of the drive mechanism is directly engaged with each set of gear teeth.

14. The surgical retractor of claim 12, further comprising:
a slot having an arcuate shape; and
a pin associated the first armature, the pin engaging the slot to limit rotation of the first armature relative to the body.

15. The surgical retractor of claim 12, further comprising:
a worm drive coupled to the first actuator, the first actuator rotatable to rotate the worm drive to operate the first armature and the second armature independent of the translatable armature; and
first and second cover plates enclosing at least a portion of the drive mechanism.

16. The surgical retractor of claim 12, wherein one or more of the first and second actuators are removable.

17. The surgical retractor of claim 12, further comprising:
a span coupleable to distal portions of the first and second armatures.

18. The surgical retractor of claim 12, further comprising:
a first blade coupleable to a distal portion of the first armature; and
a toeing screw engageable with the first armature and operable to adjust a toe angle of the first blade.

19. The surgical retractor of claim 12, wherein one of the first and second armatures and body is comprised of a radio-opaque material.

20. The surgical retractor of claim 12, wherein one of the first and second armatures and body is comprised of a radio-lucent material.

* * * * *

UNITED STATES PATENT AND TRADEMARK OFFICE
CERTIFICATE OF CORRECTION

PATENT NO. : 10,070,852 B2
APPLICATION NO. : 15/802031
DATED : September 11, 2018
INVENTOR(S) : Mast et al.

Page 1 of 1

It is certified that error appears in the above-identified patent and that said Letters Patent is hereby corrected as shown below:

On the Title Page

In item (71), in "Applicant", in Column 1, Line 2, delete "Westwinster," and insert --Westminster,-- therefor In item (57), in "Abstract", in Column 2, Lines 10-11, delete "at nature" and insert --armature-- therefor On page 2, in Column 2, item (56), under "U.S. Patent Documents", Line 12, delete "2010/0174147" and insert --2010/0174148-- therefor On page 3, in Column 1, item (56), under "Other Publications", Line 9, before "filed", insert --Response--

On page 3, in Column 1, item (56), under "Other Publications", Line 14, delete "Mar. 8, 2014"," and insert --Apr. 8, 2014",-- therefor On page 3, in Column 2, item (56), under "Other Publications", Line 19, before "filed", insert --Response--

Signed and Sealed this
Ninth Day of July, 2019

Andrei Iancu
*Director of the United States Patent and Trademark Office*